US012762695B2

(12) United States Patent
Keshwani et al.

(10) Patent No.: US 12,762,695 B2
(45) Date of Patent: Oct. 13, 2026

(54) INFORMATION PROCESSING APPARATUS, INFORMATION PROCESSING METHOD, PROGRAM, TRAINED MODEL, AND LEARNING MODEL GENERATION METHOD

(71) Applicant: FUJIFILM Corporation, Tokyo (JP)

(72) Inventors: Deepak Keshwani, Tokyo (JP); Yoshiro Kitamura, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 260 days.

(21) Appl. No.: 18/357,140

(22) Filed: Jul. 23, 2023

(65) Prior Publication Data

US 2024/0029246 A1 Jan. 25, 2024

(30) Foreign Application Priority Data

Jul. 25, 2022 (JP) ................................ 2022-118251

(51) Int. Cl.
*G06T 7/00* (2017.01)
*A61B 6/00* (2024.01)
(Continued)

(52) U.S. Cl.
CPC ............ *G06T 7/0012* (2013.01); *A61B 6/032* (2013.01); *A61B 6/482* (2013.01); *A61B 6/504* (2013.01);
(Continued)

(58) Field of Classification Search
CPC ......... A61B 6/032; A61B 6/487; A61B 6/503; A61B 6/504; A61B 6/5217; A61B 6/541;
(Continued)

(56) References Cited

U.S. PATENT DOCUMENTS

| | | | | |
|---|---|---|---|---|
| 10,753,997 | B2 * | 8/2020 | Odry .................... | G01R 33/543 |
| 2003/0199750 | A1 * | 10/2003 | Park .................... | A61B 5/0263 600/410 |

(Continued)

FOREIGN PATENT DOCUMENTS

| | | |
|---|---|---|
| JP | 2011212043 | 10/2011 |
| JP | 6746160 | 8/2020 |

OTHER PUBLICATIONS

Xu et al. "Automatic coronary artery calcium scoring on routine chest computed tomography (CT): comparison of a deep learning algorithm and a dedicated calcium scoring CT." Quantitative Imaging in Medicine and Surgery 12.5 (May 2022): 2684. (Year: 2022).*

(Continued)

*Primary Examiner* — Katrina R Fujita
(74) *Attorney, Agent, or Firm* — JCIPRNET

(57) ABSTRACT

An information processing apparatus includes one or more processors, and one or more storage devices that store a program including an image generation model trained to generate, from a first image, a second image that imitates an image obtained by an imaging protocol different from an imaging protocol of the first image. The image generation model is a model trained, through machine learning using training data in which a training image captured by a first imaging protocol is associated with a correct answer clinical parameter calculated from a corresponding image captured by a second imaging protocol different from the first imaging protocol for the same subject as the training image using a modality of the same type as a modality used to capture the training image, such that a clinical parameter calculated from a generation image output by the image generation model approaches the correct answer clinical parameter.

16 Claims, 22 Drawing Sheets

F2A

Gated image

F2B

Non-gated image

(51) Int. Cl.
*A61B 6/03* (2006.01)
*A61B 6/50* (2024.01)
*G06T 7/11* (2017.01)
*G16H 50/30* (2018.01)

(52) U.S. Cl.
CPC ............... *G06T 7/11* (2017.01); *G16H 50/30* (2018.01); *A61B 6/541* (2013.01); *G06T 2207/10081* (2013.01); *G06T 2207/20081* (2013.01); *G06T 2207/20084* (2013.01); *G06T 2207/30048* (2013.01)

(58) Field of Classification Search
CPC ..................... G06T 7/0012; G06T 7/11; G06T 2207/10081; G06T 2207/20081; G06T 2207/20084; G06T 2207/30048; G16H 50/30
See application file for complete search history.

(56) References Cited

U.S. PATENT DOCUMENTS

| | | | | |
|---|---|---|---|---|
| 2010/0220909 | A1* | 9/2010 | Thielemans | G06T 11/005 382/131 |
| 2011/0245651 | A1 | 10/2011 | Nakamura | |
| 2015/0192653 | A1* | 7/2015 | Sharif | G06T 11/003 600/420 |
| 2020/0160509 | A1* | 5/2020 | Pack | G16H 30/40 |
| 2021/0035340 | A1* | 2/2021 | Wang | G16H 50/50 |
| 2021/0257094 | A1 | 8/2021 | Takemoto et al. | |
| 2021/0319557 | A1* | 10/2021 | Gooding | A61B 6/5217 |
| 2021/0319558 | A1* | 10/2021 | Min | A61K 49/04 |
| 2022/0375073 | A1* | 11/2022 | Voigt | G06T 5/92 |
| 2022/0405915 | A1* | 12/2022 | Gordon | G06T 7/10 |
| 2025/0111516 | A1* | 4/2025 | Slomka | G06T 7/11 |

OTHER PUBLICATIONS

Tang et al. "Contrast phase classification with a generative adversarial network." Medical Imaging 2020: Image Processing. vol. 11313. SPIE, 2020. (Year: 2020).*

"Search Report of Europe Counterpart Application", issued on Dec. 12, 2023, p. 1-p. 12.

Sanne G. M. Van Velzen et al., "Generative models for reproducible coronary calcium scoring", Journal of Medical Imaging, vol. 9, May 2022, pp. 1-19.

Asmae Mama Zair et al., "Machine learning for coronary artery calcification detection and labeling using only native computer tomography", Physical and Engineering Sciences in Medicine, vol. 45, Nov. 2021, pp. 49-61.

Juan C. Montoya et al., "Reconstruction of three-dimensional tomographic patient models for radiation dose modulation in CT from two scout views using deep learning", Medical Physics, vol. 49, Jan. 2022, pp. 901-916.

David Eng et al., "Automated coronary calcium scoring using deep learning with multicenter external validation," NPJ Digital Medicine, Jun. 2021, pp. 1-13.

"Notice of Reasons for Refusal of Japan Counterpart Application", issued on Mar. 19, 2026, with English translation thereof, p. 1-p. 10.

"Decision of Refusal of Japan Counterpart Application", issued on Jun. 12, 2026, with English translation thereof, pp. 1-13.

* cited by examiner

Gated image

Non-gated image

Gated image
(Calcium region > 100 HU)

| Branch | Score* |
|---|---|
| RCA | 0 |
| LM | 0 |
| LAD | 90 |
| LCx | 30 |
| Total | 120 |

F4A

Non-gated image

| Branch | Score* |
| --- | --- |
| RCA | 0 |
| LM | 0 |
| LAD | 40 |
| LCx | 10 |
| Total | 50 |

FIG. 11

| NUMBER | TRAINING DATA SET | |
|---|---|---|
| | FOR INPUT | TEACHER |
| 1 | NON-ELECTROCARDIOGRAM GATED CT IMAGE | CAC SCORE |
| 2 | NON-ELECTROCARDIOGRAM GATED CT IMAGE | CAC SCORE |
| ⋮ | ⋮ | ⋮ |
| j | NON-ELECTROCARDIOGRAM GATED CT IMAGE ~TIj | CAC SCORE ~GTj |
| ⋮ | ⋮ | ⋮ |

INFORMATION PROCESSING APPARATUS, INFORMATION PROCESSING METHOD, PROGRAM, TRAINED MODEL, AND LEARNING MODEL GENERATION METHOD

CROSS-REFERENCE TO RELATED APPLICATION

The present application claims priority under 35 U.S.C § 119(a) to Japanese Patent Application No. 2022-118251 filed on Jul. 25, 2022, which is hereby expressly incorporated by reference, in its entirety, into the present application.

BACKGROUND OF THE INVENTION

1. Field of the Invention

The present disclosure relates to an information processing apparatus, an information processing method, a program, a trained model, and a learning model generation method, and particularly relates to an image processing technology and a machine learning technology of calculating a clinical parameter from a medical image.

2. Description of the Related Art

As a common method of detecting a cardiovascular disease (CVD), a computed tomography (CT) image of a chest region is captured to quantify the calcification of a coronary artery and the heart. Coronary artery calcification (CAC) scoring is the most characteristic and standard marker in the detection of the CVD. The severity of the CVD is evaluated based on the CAC score, and treatment or the like is prescribed. At present, in a case of measuring the CAC score, an electrocardiogram gated CT (ECG gated CT) image obtained by a special electrocardiogram (ECG) gated imaging method is used in order to eliminate movement artifacts of the heart.

On the other hand, Eng, D., Chute, C., Khandwala, N. et al. "Automated coronary calcium scoring using deep learning with multicenter external validation." npj Digit. Med. 4, 88 (2021) discloses a technology of performing class-classification of the CAC severity into four stages with limited accuracy from a non-electrocardiogram gated CT (non ECG gated CT) image obtained by a non-electrocardiogram gated imaging method. In the method described in Eng, D., Chute, C., Khandwala, N. et al. "Automated coronary calcium scoring using deep learning with multicenter external validation." npj Digit. Med. 4, 88 (2021), first, a convolutional neural network (CNN) is used to segment a calcium region from the non-electrocardiogram gated CT image. Next, feature amounts, such as an average CT value and a standard deviation, are acquired from the segmented calcium region, and another machine learning method is used to train a model to output the same CAC severity stage as the severity stage grasped in the corresponding electrocardiogram gated CT image.

In addition, with respect to the image diagnosis support technology, JP6746160B discloses a system that, in view of the disadvantages of images captured by using radioactive drugs, such as positron emission tomography (PET) images, estimates an image, such as the PET image using the drug, from images, such as a magnetic resonance imaging (MRI) image that can be captured without using the radioactive drugs, and utilizes the estimated image for diagnosis. The system disclosed in JP6746160B includes an acquisition unit that acquires examinee information including real image data of an MR image of an examinee including at least a reference region partially including an evaluation target region, and an information providing unit that, by an image processing model subjected to machine learning to generate a pseudo PET image data of the evaluation target region from the real image data of the MR images of the reference regions based on training data including real image data of the MR images of the reference regions of a plurality of test subjects and the real image data of the PET image including the evaluation target region, provides diagnosis support information based on the pseudo PET image data of the evaluation target region generated from the real image data of the individual MR image of the examinee.

SUMMARY OF THE INVENTION

Although the electrocardiogram gated imaging can obtain a finer image than the non-electrocardiogram gated imaging, the imaging method is complicated and a special imaging system is required. In addition, in the electrocardiogram gated imaging, a radiation dose to a subject is increased as compared with the non-electrocardiogram gated imaging. From the viewpoint of reducing the radiation dose and reducing a load on the subject, it is desirable to measure the CAC score by using a normal chest CT image used for screening for lung cancer or respiratory disease.

However, the normal non-electrocardiogram gated CT image obtained by the non-electrocardiogram gated imaging is an unclear (blurred) image due to the movement of the heart, and it is difficult to accurately measure the CAC score from the non-electrocardiogram gated CT image. Therefore, it is desired to develop a technology of performing CAC scoring with sufficient accuracy from the non-electrocardiogram gated CT image.

In this regard, in Eng, D., Chute, C., Khandwala, N. et al. "Automated coronary calcium scoring using deep learning with multicenter external validation." npj Digit. Med. 4, 88 (2021), although the CAC severity stage can be estimated by using the non-electrocardiogram gated CT image, the CAC score cannot be calculated with the same level of accuracy as the electrocardiogram gated CT image. In addition, the method of calculating the CAC severity described in Eng, D., Chute, C., Khandwala, N. et al. "Automated coronary calcium scoring using deep learning with multicenter external validation." npj Digit. Med. 4, 88 (2021) is a black box method using so-called unexplainable artificial intelligence (AI) in which it is not possible to describe how (why) the result is derived.

The above-described problems are not limited to the CT image and the CAC score, but are common problems in a case of calculating various clinical parameters using images of other modalities. To solve such problems, there is a demand for a technology that can achieve the same diagnosis accuracy as the images that can only be acquired by a complex imaging method, an imaging method that requires an expensive high-performance imaging system, or an imaging method that imposes a large load on the subject, from images that can be acquired more simply, inexpensively, or with a low load.

The present disclosure has been made in view of such circumstances, and is to provide an information processing apparatus, an information processing method, a program, a trained model, and a learning model generation method capable of accurately calculating a clinical parameter from an image that can be acquired relatively easily or with a low load.

A first aspect of the present disclosure relates to an information processing apparatus comprising one or more processors, and one or more storage devices that store a program to be executed by the one or more processors, in which the program includes an image generation model trained to generate, from a first image which is input, a second image that imitates an image obtained by an imaging protocol different from an imaging protocol of the first image, the image generation model is a model trained, through machine learning using a plurality of training data in which a training image captured by a first imaging protocol is associated with a correct answer clinical parameter calculated from a corresponding image captured by a second imaging protocol different from the first imaging protocol for the same subject as the training image using a modality of the same type as a modality used to capture the training image, such that a clinical parameter calculated from a generation image output by the image generation model in response to input of the training image approaches the correct answer clinical parameter, and the one or more processors receive input of the first image captured by the first imaging protocol, generate the second image from the first image by the image generation model, and calculate the clinical parameter from the second image.

The term "imaging protocol" includes the concept of terms, such as an imaging method, an imaging condition, and a scan setting.

According to the present disclosure, it is possible to calculate the clinical parameter from the first image captured by the first imaging protocol with the same level of accuracy as the image captured by the second imaging protocol of the same type of modality. The first imaging protocol may be an imaging method that is simpler than the second imaging protocol, and can be a system that is cheaper than a system required for imaging of the second imaging protocol. Also, the first imaging protocol can have a lower load on the subject than the second imaging protocol.

A second aspect relates to the information processing apparatus according to the first aspect, in which the one or more processors may divide the first image into anatomical regions, and may calculate the clinical parameter for each of the divided anatomical regions.

A third aspect relates to the information processing apparatus according to the second aspect, in which each of the training image and the corresponding image may be divided into the anatomical regions, and the correct answer clinical parameter is calculated for each of the divided anatomical regions of the corresponding image, and the image generation model may be a model trained such that each clinical parameter calculated from the generation image for each of the divided anatomical regions of the training image approaches the correct answer clinical parameter of each of the divided anatomical regions of the corresponding image.

A fourth aspect relates to the information processing apparatus according to the second or third aspect, in which the divided anatomical region may be a perfusion region of a coronary artery.

A fifth aspect relates to the information processing apparatus according to any one of the second to fourth aspects, in which the clinical parameter may be a calcium volume for each main branch of a coronary artery.

A sixth aspect relates to the information processing apparatus according to any one of the first to fifth aspects, in which the first image may be a non-electrocardiogram gated CT image obtained by non-electrocardiogram gated imaging, and the second image may be an image that imitates an electrocardiogram gated CT image obtained by electrocardiogram gated imaging.

A seventh aspect relates to the information processing apparatus according to any one of the first to sixth aspects, in which the training image may be captured under a condition of a lower dose than the corresponding image.

An eighth aspect relates to the information processing apparatus according to any one of the first to sixth aspects, in which the first imaging protocol may have a lower dose than the second imaging protocol.

A ninth aspect relates to the information processing apparatus according to any one of the first to eighth aspects, in which the first imaging protocol may have a slower scan speed than the second imaging protocol.

A tenth aspect relates to the information processing apparatus according to any one of the first to ninth aspects, in which the clinical parameter may be a calcification score.

An eleventh aspect relates to the information processing apparatus according to any one of the first to ninth aspects, in which the clinical parameter may be a cardiovascular calcium volume.

A twelfth aspect relates to the information processing apparatus according to any one of the first to ninth aspects, in which the clinical parameter may be severity of coronary artery calcification.

A thirteenth aspect relates to the information processing apparatus according to any one of the first to twelfth aspects, in which the image generation model may be configured by a neural network.

A fourteenth aspect relates to an information processing method executed by one or more processors, the method comprising, via the one or more processors, acquiring a first image captured by a first imaging protocol, inputting the first image to an image generation model and generating, from the first image by the image generation model, a second image that imitates an image obtained in a case in which imaging is performed by a second imaging protocol different from the first imaging protocol for the same subject as the first image using a modality of the same type as a modality used to capture the first image, and calculating a clinical parameter from the second image, in which the image generation model is a model trained, by using a plurality of training data in which a training image captured by the first imaging protocol is associated with a correct answer clinical parameter calculated from a corresponding image captured by the second imaging protocol for the same subject as the training image using a modality of the same type as a modality used to capture the training image, such that the clinical parameter calculated from a generation image output by the image generation model in response to input of the training image approaches the correct answer clinical parameter.

The information processing method according to the fourteenth aspect can be configured to include the specific aspect similar to that of the information processing apparatus according to any one of the second to thirteenth aspects.

A fifteenth aspect relates to a program causing a computer to realize a function of acquiring a first image captured by a first imaging protocol, a function of inputting the first image to an image generation model and generating, from the first image by the image generation model, a second image that imitates an image obtained in a case in which imaging is performed by a second imaging protocol different from the first imaging protocol for the same subject as the first image using a modality of the same type as a modality used to capture the first image, and a function of calculating a clinical parameter from the second image, in which the image generation model is a model trained, through machine learning using a plurality of training data in which a training image captured by the first imaging protocol is associated with a correct answer clinical parameter calculated from a corresponding image captured by the second imaging protocol for the same subject as the training image using a modality of the same type as a modality used to capture the training image, such that the clinical parameter calculated from a generation image output by the image generation model in response to input of the training image approaches the correct answer clinical parameter.

The program according to the fifteenth aspect can be configured to include the specific aspect similar to that of the information processing apparatus according to any one of the second to thirteenth aspects.

A sixteenth aspect relates to a trained model that enables a computer to realize a function of generating, from an image which is input, a pseudo image that imitates an image obtained by an imaging protocol different from an imaging protocol of the image, in which the trained model has been trained, through machine learning using a plurality of training data in which a training image captured by a first imaging protocol is associated with a correct answer clinical parameter calculated from a corresponding image captured by a second imaging protocol different from the first imaging protocol for the same subject as the training image using a modality of the same type as a modality used to capture the training image, such that a clinical parameter calculated from a generation image output by a learning model in response to input of the training image approaches the correct answer clinical parameter.

The trained model according to the sixteenth aspect can be configured to include the specific aspect similar to that of the information processing apparatus according to any one of the second to thirteenth aspects.

A seventeenth aspect relates to a learning model generation method of generating a learning model that enables a computer to realize a function of generating, from an image which is input, a pseudo image that imitates an image obtained by an imaging protocol different from an imaging protocol of the image, the method comprising, via a system including one or more processors, performing machine learning using a plurality of training data in which a training image captured by a first imaging protocol is associated with a correct answer clinical parameter calculated from a corresponding image captured by a second imaging protocol different from the first imaging protocol for the same subject as the training image using a modality of the same type as a modality used to capture the training image, and inputting the training image to the learning model, calculating a clinical parameter from a generation image output from the learning model, and training the learning model such that the clinical parameter calculated from the generation image approaches the correct answer clinical parameter.

The learning model generation method according to the seventeenth aspect can be configured to include the specific aspect similar to that of the information processing apparatus according to any one of the second to thirteenth aspects.

According to the present disclosure, it is possible to calculate the clinical parameter based on the first image captured by the first imaging protocol with the same level of accuracy as the image captured by the second imaging protocol of the same type of modality. Accordingly, it is possible to achieve the same diagnosis accuracy as the diagnosis accuracy based on the image captured by the second imaging protocol from the image captured by the first imaging protocol. The first imaging protocol can be the imaging method that is simpler than the second imaging protocol, and can be the system that is cheaper than the system required for imaging of the second imaging protocol. Also, the first imaging protocol can have a lower load on the subject than the second imaging protocol.

BRIEF DESCRIPTION OF THE DRAWINGS

FIG. 11 is a conceptual diagram of a training data set.

DESCRIPTION OF THE PREFERRED EMBODIMENTS

Hereinafter, the description of preferred embodiments of the present invention will be made in detail with reference to the accompanying drawings.

Description of CAC Scoring

Figure 1:
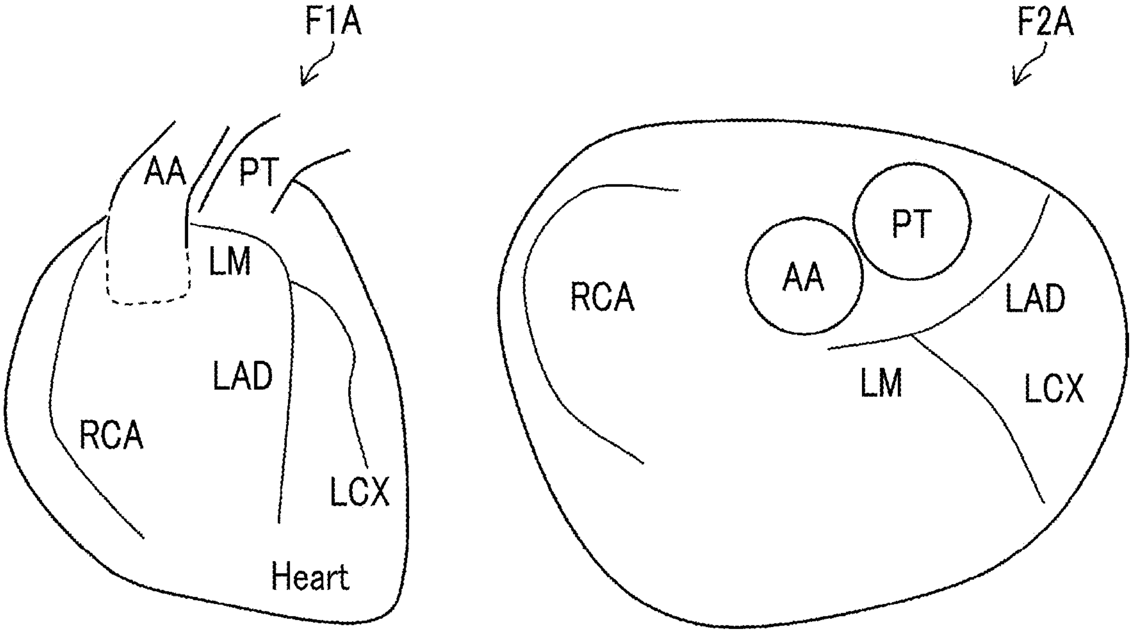
FIG. 1 is an explanatory diagram schematically showing a heart and a coronary artery.

Here, as an example, a case will be described in which a CAC score is measured from a CT image obtained by imaging a chest region including a heart of a subject using a CT apparatus. The CT apparatus is an example of a modality that captures a medical image. A CAC score is an example of a clinical parameter used for diagnosis. FIG. 1 is an explanatory diagram schematically showing the heart and a coronary artery. A left figure F1A of FIG. 1 is a front view of the heart, and a right figure FIB of FIG. 1 is a view of the heart from above. The coronary artery includes four main branches of a left main coronary trunk (LM), a left anterior descending artery (LAD), a left circumflex artery (LCX), and a right coronary artery (RCA). In FIG. 1, "AA" represents an ascending aorta, and "PT" represents a pulmonary artery trunk.

In the CAC scoring, an amount of calcium deposition in these four main branches of the coronary artery is measured. The calcium in the coronary artery is a factor that causes a heart disease. A risk of the heart disease has a correlation with a total CAC score obtained by totaling the amount of calcium in each main branch in the coronary artery, and a treatment method or the like is decided based on the calculated CAC score.

Figure 2:
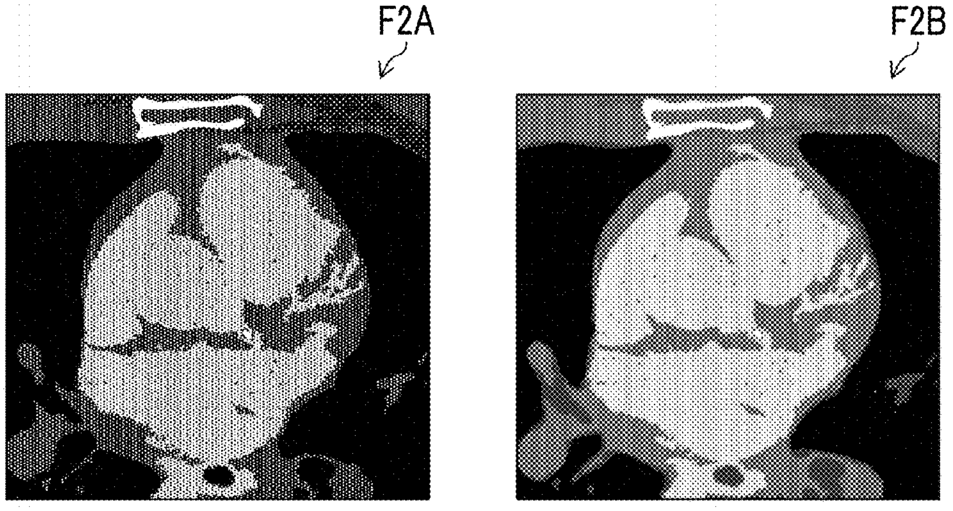
FIG. 2 is an example of a CT image in which a chest region including the heart is imaged.

FIG. 2 is an example of the CT image in which the chest region including the heart is imaged. An image F2A on the left side of FIG. 2 is an example of an electrocardiogram gated CT image obtained by electrocardiogram gated imaging. An image F2B on the right side of FIG. 2 is an example of a non-electrocardiogram gated CT image obtained by non-electrocardiogram gated imaging for the same subject. As is clear from a comparison between both images, the electrocardiogram gated CT image (left figure) is the fine image F2A in which the influence of the movement of the heart is suppressed, whereas the non-electrocardiogram gated CT image (right figure) is the unclear (blurred) image F2B due to the movement of the heart during imaging. It should be noted that both the non-electrocardiogram gated CT image and the electrocardiogram gated CT image are three-dimensional images composed of three-dimensional data obtained by continuously capturing two-dimensional slice tomographic images. The term "image" includes the meaning of image data.

The electrocardiogram gated imaging is an example of a "first imaging protocol" according to the present disclosure. The non-electrocardiogram gated imaging is an example of a "second imaging protocol" according to the present disclosure. The electrocardiogram gated CT image and the non-electrocardiogram gated CT image are examples of an image captured by using the same type of modality.

The non-electrocardiogram gated CT image can be captured under a condition of a lower dose than the electrocardiogram gated CT image. That is, the non-electrocardiogram gated imaging is an imaging method in which imaging can be performed at a lower dose than the electrocardiogram gated imaging and has less load on the subject. In addition, the non-electrocardiogram gated CT image can be captured at a slower scan speed than the electrocardiogram gated CT image.

Description of Problem

Figure 3:
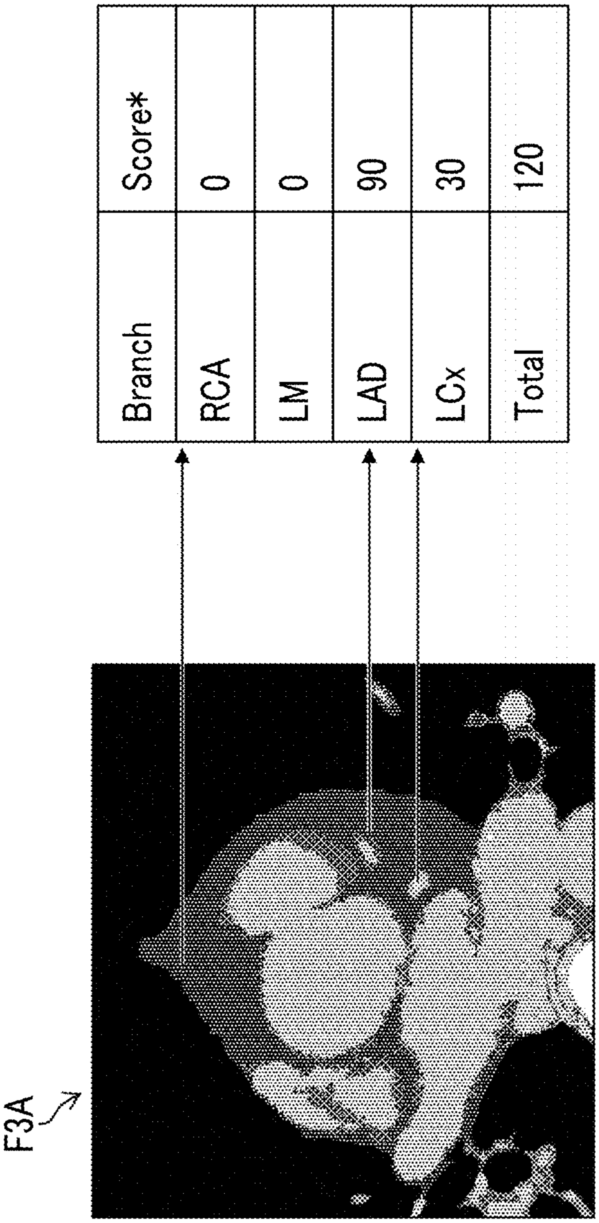
FIG. 3 is an explanatory diagram showing an example of a CAC score measured from an electrocardiogram gated CT image.

FIG. 3 is an explanatory diagram showing an example of a CAC score measured from an electrocardiogram gated CT image F3A. In the electrocardiogram gated CT image F3A, a region of the heart is divided into a perfusion region (dominant region) of each of the four main branches, and the CAC score is calculated for each region of the main branch. The identification of the perfusion region of each main branch may be automatically performed by image processing using, for example, a segmentation model trained by machine learning, or a doctor may manually designate the region while observing the image. The identification as to whether or not the region is a calcium region can be determined by performing threshold value processing on a CT value of each voxel. For example, a region having a CT value greater than 100 HU is determined as the calcium region.

In the example shown in FIG. 3, an example is shown in which the individual CAC scores of coronary artery branches of the RCA, LM, LAD, and LCX are calculated as "0", "0", "90", and "30", respectively, and the total CAC score is calculated as "120".

Figure 4:
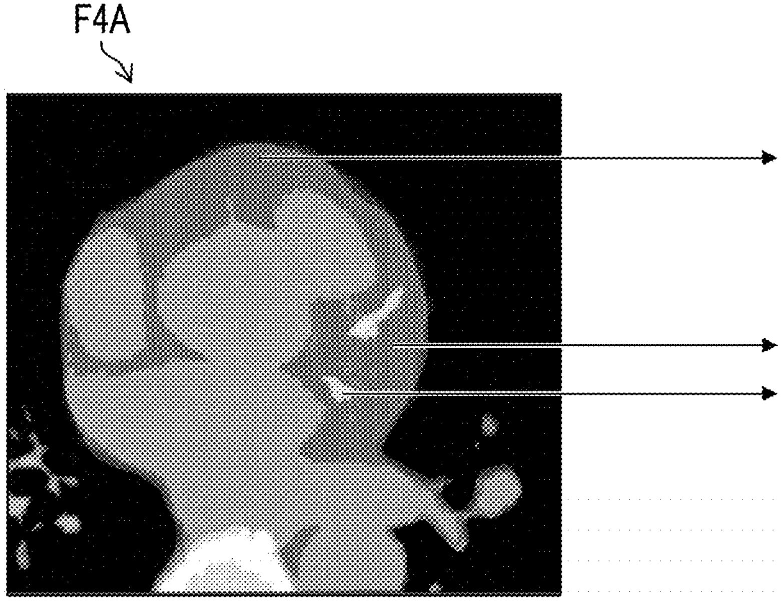
FIG. 4 is an explanatory diagram showing an example of a CAC score measured from a non-electrocardiogram gated CT image of the same subject as the electrocardiogram gated CT image shown in FIG. 3.

FIG. 4 is an explanatory diagram showing an example of a CAC score measured from a non-electrocardiogram gated CT image F4A of the same subject as the electrocardiogram gated CT image F3A shown in FIG. 3. For the non-electrocardiogram gated CT image F4A shown in FIG. 4, an example is shown in which, in a case in which the CAC score for each region of the coronary artery branch is calculated by performing the threshold value processing of the CT value similarly to the electrocardiogram gated CT image F3A of FIG. 3, the individual CAC scores of coronary artery branches of the RCA, LM, LAD, and LCX are calculated as "0", "0", "40", and "10", respectively, and the total CAC score is calculated as "50". The total CAC score is an example of a "calcification score" according to the present disclosure.

As shown in FIG. 4, the CAC score calculated from the non-electrocardiogram gated CT image F4A deviates from the CAC score calculated from the electrocardiogram gated CT image F3A, and it is difficult to correctly (accurately) calculate the CAC score from the non-electrocardiogram gated CT image F4A with the same level of accuracy as the electrocardiogram gated CT image F3A.

It should be noted that, in FIG. 3 and FIG. 4, the individual CAC score is calculated for each of the perfusion regions of the four main branches, and the total CAC score is obtained from the total of these CAC scores. However, the CAC score may be calculated by counting the number of voxels having a CT value equal to or greater than 100 HU from the entire heart without the division for each the perfusion region of the main branch. It should be noted that “100 HU” is an example of a threshold value for determining the calcium region.

First Embodiment

Configuration of Information Processing Apparatus

Figure 5:
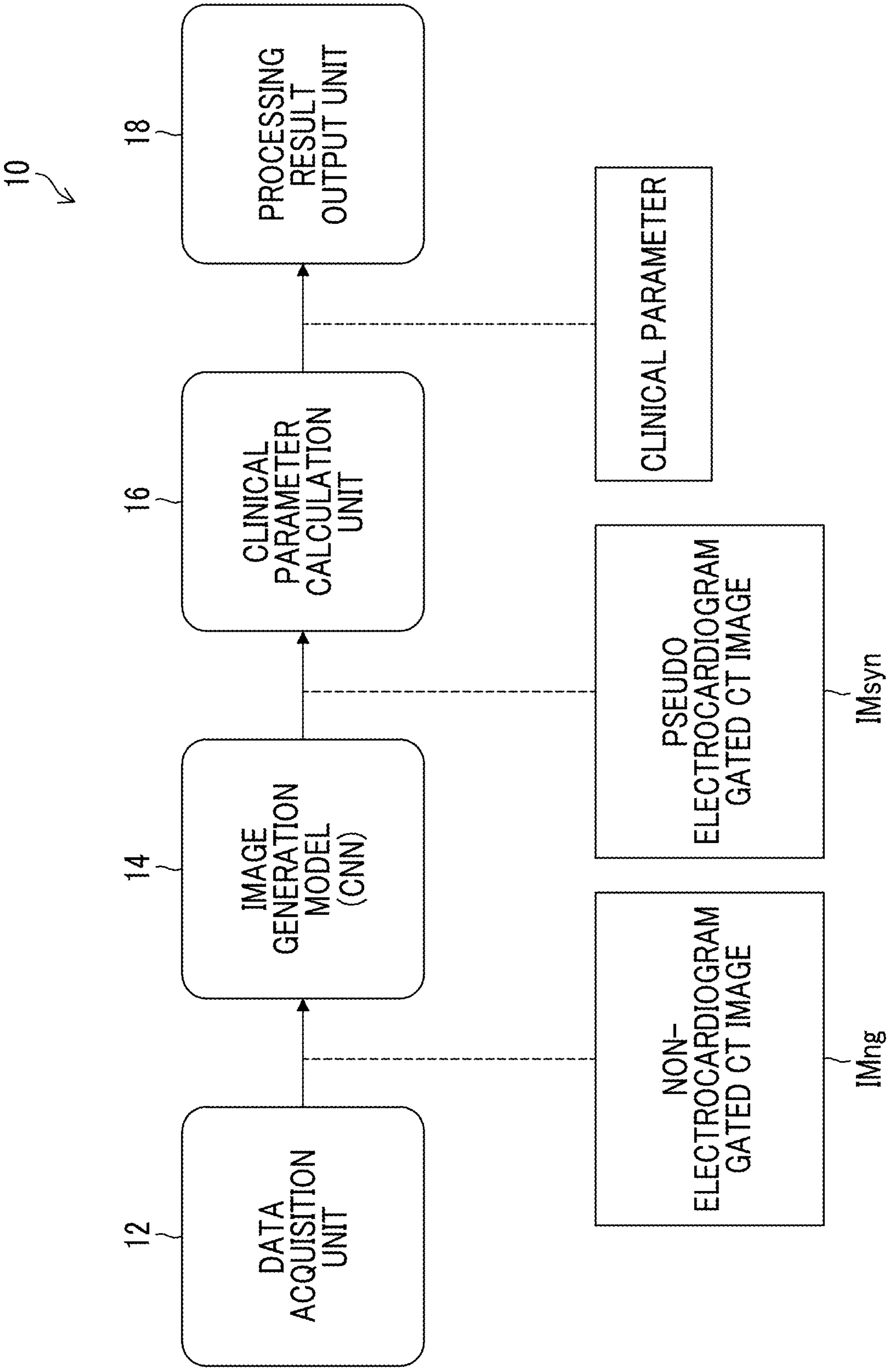
FIG. 5 is a block diagram showing a functional configuration of an information processing apparatus according to a first embodiment.

FIG. 5 is a block diagram showing a functional configuration of an information processing apparatus 10 according to a first embodiment. The information processing apparatus 10 comprises a data acquisition unit 12, an image generation model 14, a clinical parameter calculation unit 16, and a processing result output unit 18. Various functions of the information processing apparatus 10 can be realized by a combination of hardware and software of a computer. The information processing apparatus 10 may be configured by a computer system including one or a plurality of computers.

The data acquisition unit 12 acquires a non-electrocardiogram gated CT image IMng as a processing target. The non-electrocardiogram gated CT image IMng input via the data acquisition unit 12 is data of a real image obtained by actually imaging the subject using the CT apparatus.

The image generation model 14 is a trained model trained, through machine learning, to generate a pseudo electrocardiogram gated CT image IMsyn from the non-electrocardiogram gated CT image IMng in response to input of the non-electrocardiogram gated CT image IMng. The image generation model 14 is configured by using a structure of a fully convolutional neural network (FCN), which is a so-called encoder-decoder type.

The pseudo electrocardiogram gated CT image IMsyn output from the image generation model 14 is a synthetic image artificially generated by the image processing for use in the calculation of the CAC score. The pseudo electrocardiogram gated CT image IMsyn is an intermediate image that is intermediately generated in a process of processing of predicting the CAC score based on the input non-electrocardiogram gated CT image IMng. The pseudo electrocardiogram gated CT image IMsyn is generated as an artificial image that imitates the electrocardiogram gated CT image obtained by the electrocardiogram gated imaging. However, the target CAC score need only be accurately calculated from this pseudo image (intermediate image), and it does not matter whether or not the pseudo image itself is similar to features of the electrocardiogram gated CT image of the real image obtained by the actual electrocardiogram gated imaging. It should be noted that the term “pseudo image” may be paraphrased as “correction image” or “conversion image”.

The non-electrocardiogram gated CT image IMng is an example of a “first image” according to the present disclosure, and the pseudo electrocardiogram gated CT image IMsyn is an example of a “second image” according to the present disclosure.

The image generation model 14 is a model trained such that, by using training data in which the non-electrocardiogram gated CT image as the training image is associated with a correct answer CAC score calculated from the electrocardiogram gated CT image of the same subject as the training image, the CAC score calculated from an output image (pseudo image) output by the model in response to the input of the training image approaches the correct answer CAC score. Details of the machine learning method of obtaining the image generation model 14 will be described below.

The clinical parameter calculation unit 16 calculates a clinical parameter for diagnosis based on the pseudo electrocardiogram gated CT image IMsyn generated by the image generation model 14. The clinical parameter that is a calculation target in the present embodiment is the CAC score.

The processing result output unit 18 outputs a processing result including a value of the clinical parameter (calculation result of the clinical parameter) calculated by the clinical parameter calculation unit 16. The processing result output unit 18 may be configured to perform at least one of a processing of displaying the processing result, a processing of recording the processing result in a database or the like, or a processing of printing the processing result, for example.

Figure 6:
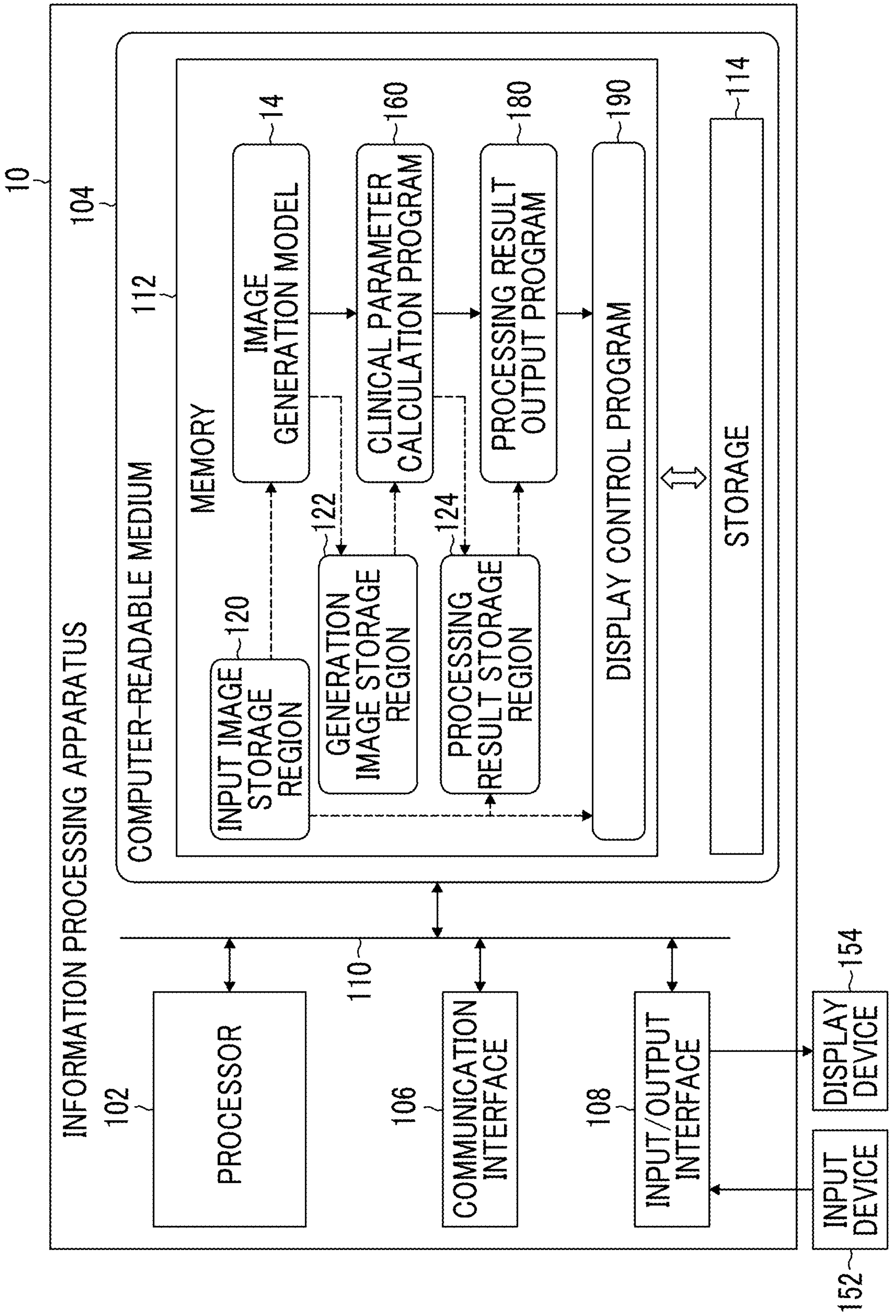
FIG. 6 is a block diagram showing an example of a hardware configuration of the information processing apparatus according to the first embodiment.

FIG. 6 is a block diagram showing an example of a hardware configuration of the information processing apparatus 10. The information processing apparatus 10 comprises a processor 102, a computer-readable medium 104, which is a non-transitory tangible object, a communication interface 106, an input/output interface 108, and a bus 110. The processor 102 is connected to the computer-readable medium 104, the communication interface 106, and the input/output interface 108 via the bus 110. A form of the information processing apparatus 10 is not particularly limited, and may be a server, a personal computer, a workstation, a tablet terminal, and the like. In addition, the information processing apparatus 10 may be a viewer terminal or the like for image interpretation.

The processor 102 includes a central processing unit (CPU). The processor 102 may include a graphics processing unit (GPU). The computer-readable medium 104 includes a memory 112 which is a main storage device, and a storage 114 which is an auxiliary storage device. For example, the computer-readable medium 104 may be a semiconductor memory, a hard disk drive (HDD) device, a solid state drive (SSD) device, or a combination of a plurality of semiconductor memories, HDD devices, and SSD devices. The computer-readable medium 104 is an example of a “storage device” according to the present disclosure.

The computer-readable medium 104 includes an input image storage region 120, a generation image storage region 122, and a processing result storage region 124. In addition, the computer-readable medium 104 stores a plurality of programs, data, and the like including the image generation model 14, a clinical parameter calculation program 160, a processing result output program 180, and a display control program 190. The term “program” includes the concept of a program module. The processor 102 functions as various processing units by executing an instruction of the program stored in the computer-readable medium 104.

The non-electrocardiogram gated CT image IMng input as a target image for processing is stored in the input image storage region 120. The pseudo electrocardiogram gated CT image IMsyn, which is a generation image output from the image generation model 14, is stored in the generation image storage region 122. The clinical parameter calculation program 160 includes an instruction to execute processing of calculating the clinical parameter from the pseudo electrocardiogram gated CT image IMsyn. The information on the processing result including the value of the clinical parameter calculated by the clinical parameter calculation program 160 is recorded in the processing result storage region 124.

The processing result output program 180 includes an instruction to execute processing of outputting the processing result including the value of the clinical parameter. The display control program 190 includes an instruction to generate a display signal required for display output to a display device 154 and execute display control of the display device 154.

The information processing apparatus 10 can be connected to an electric telecommunication line (not shown) via the communication interface 106. The electric telecommunication line may be a wide area communication line, a premises communication line, or a combination thereof.

The information processing apparatus 10 may comprise an input device 152 and the display device 154. For example, the input device 152 is configured by a keyboard, a mouse, a multi touch panel, or other pointing devices, a voice input device, or an appropriate combination thereof. For example, the display device 154 is configured by a liquid crystal display, an organic electro-luminescence (OEL) display, a projector, or an appropriate combination thereof. The input device 152 and the display device 154 are connected to the processor 102 via the input/output interface 108.

Outline of Machine Learning Method

Figure 7:
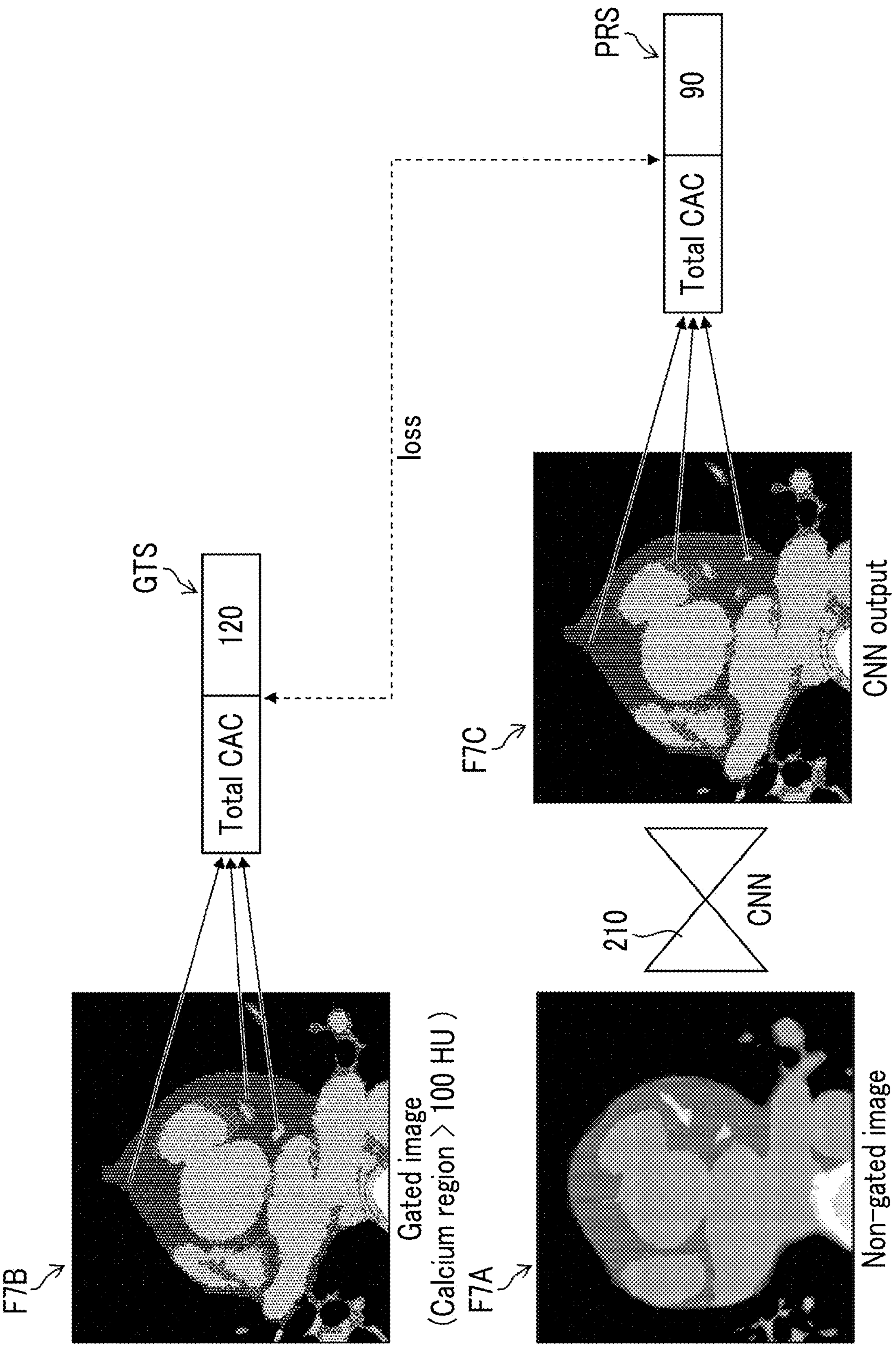
FIG. 7 is an explanatory diagram showing an outline of a machine learning method of generating an image generation model applied to the first embodiment.

FIG. 7 is an explanatory diagram showing an outline of a machine learning method of generating the image generation model 14 applied to the first embodiment.

A data set used for the training includes a plurality of training data in which a non-electrocardiogram gated CT image F7A obtained by imaging the subject is associated with a CAC score GTS calculated from an electrocardiogram gated CT image F7B obtained by imaging the same subject as the non-electrocardiogram gated CT image F7A. The non-electrocardiogram gated CT image F7A is a training image for input to a learning model 210. The CAC score GTS is a correct answer CAC score corresponding to the non-electrocardiogram gated CT image F7A, and corresponds to teacher data (correct answer data) in supervised learning. The CAC score GTS may be, for example, a value obtained by counting the number of voxels in a region in which the CT value in the electrocardiogram gated CT image F7B is greater than 100 HU. In a case of the first embodiment, the CAC score GTS may be the total CAC score. The electrocardiogram gated CT image F7B is an example of a "corresponding image" according to the present disclosure.

The learning model 210 is configured by a fully convolutional neural network and is trained through the following method.

[Procedure 1] The non-electrocardiogram gated CT image F7A, which is the training image, is input to the learning model 210.

[Procedure 2] The output of a generation image F7C is obtained from the learning model 210 by inputting the non-electrocardiogram gated CT image F7A.

[Procedure 3] A CAC score PRS is calculated for the generation image F7C output from the learning model 210 by performing the threshold value processing under the condition in which CT value >100 HU. The CAC score PRS calculated from the generation image F7C is a CAC score predicted from the non-electrocardiogram gated CT image F7A.

[Procedure 4] A machine learning device including a processor that executes processing of the machine learning calculates a loss from the CAC score PRS calculated from the generation image F7C and the CAC score GTS of the correct answer, and updates a model parameter of the learning model 210 such that the loss is minimized. The loss may be an L1 loss, for example. It should be noted that the learning in which the loss is minimized means learning in which the CAC score PRS calculated from the generation image F7C approaches the CAC score GTS of the correct answer (such that an error is reduced).

By repeating the above procedures 1 to 4 using the plurality of training data, the model parameter of the learning model 210 is optimized, and the learning model 210 is trained to generate the generation image F7C in which the CAC score PRS is calculated with the same level of accuracy as the correct answer CAC score.

Figure 8:
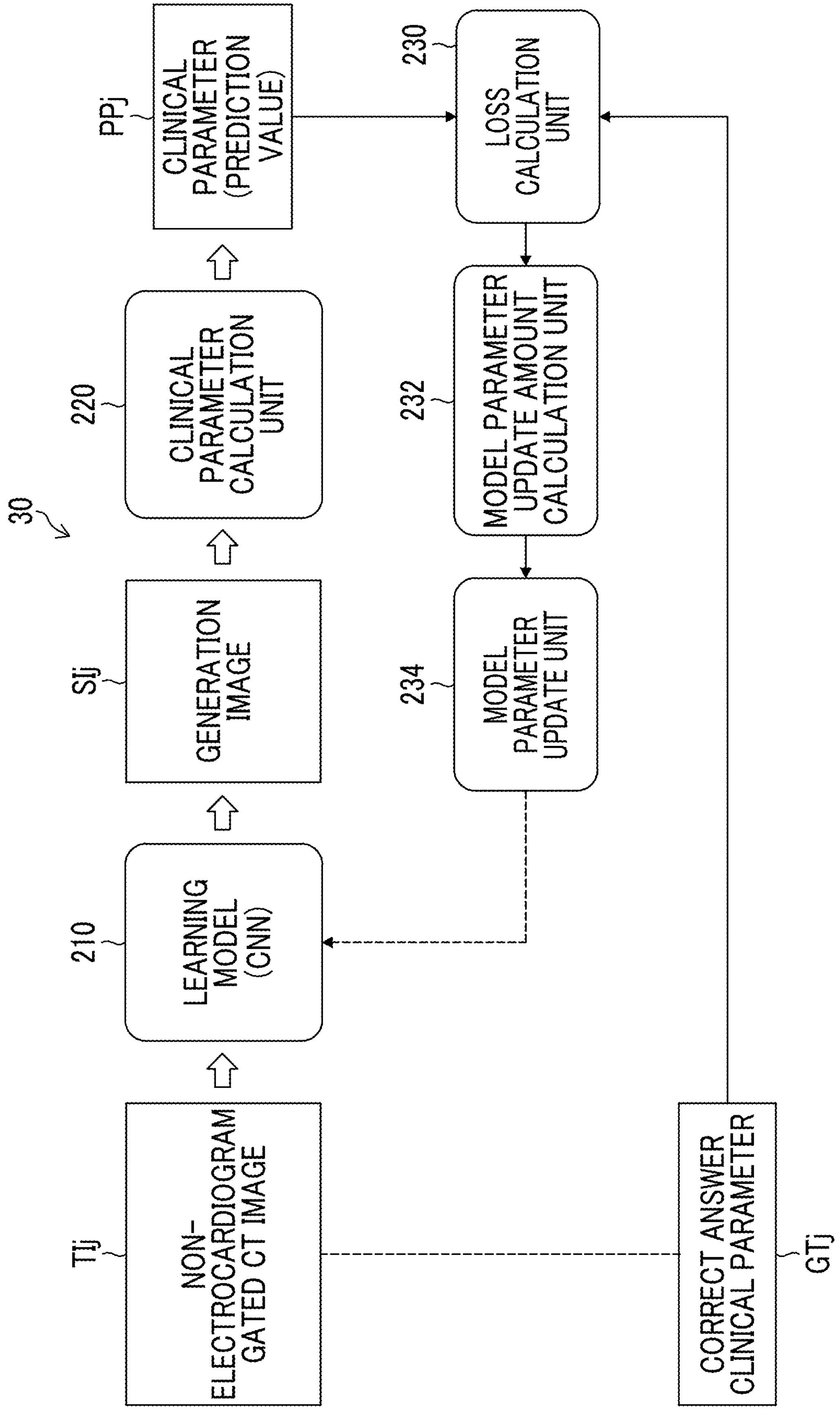
FIG. 8 is a block diagram showing a functional configuration of a machine learning device applied to the first embodiment.

FIG. 8 is a block diagram showing a functional configuration of a machine learning device 30. The machine learning device 30 includes a learning model 210, a clinical parameter calculation unit 220, a loss calculation unit 230, a model parameter update amount calculation unit 232, and a model parameter update unit 234. A function of each processing unit of the machine learning device 30 can be realized by a combination of hardware and software of the computer. The functions of the respective units of the machine learning device 30 may be realized by one computer, or the processing functions may be shared and realized by two or more plurality of computers.

The training data includes a training image TIj, which is the non-electrocardiogram gated CT image, and a correct answer clinical parameter GTj corresponding to the training image TIj. A subscript j represents an index number that identifies the plurality of training data. In a case of the first embodiment, the correct answer clinical parameter GTj may be a CAC score calculated from the electrocardiogram gated CT image of the same subject as the training image TIj.

The learning model 210 outputs a generation image SIj in response to the input of the training image TIj, which is the non-electrocardiogram gated CT image. The clinical parameter calculation unit 220 calculates a clinical parameter PPj from the generation image SIj. The clinical parameter PPj may be a total CAC score calculated from the generation image SIj by threshold value processing. The clinical parameter PPj calculated from the generation image SIj corresponds to a clinical parameter prediction value which is predicted (estimated) from the training image TIj.

The loss calculation unit 230 calculates a loss indicating an error between the clinical parameter PPj calculated by the clinical parameter calculation unit 220 and the correct answer clinical parameter GTj.

The model parameter update amount calculation unit 232 calculates an update amount of the model parameter in the learning model 210 based on the calculated loss. The model parameter includes a filter coefficient (weight of coupling between nodes) of a filter used for processing each layer of the CNN, a bias of the nodes, and the like.

The model parameter update unit 234 updates the model parameter of the learning model 210 according to the update amount calculated by the model parameter update amount calculation unit 232. The model parameter update amount calculation unit 232 and the model parameter update unit 234 optimize the model parameter by, for example, a method such as a stochastic gradient descent (SGD) method.

Figure 9:
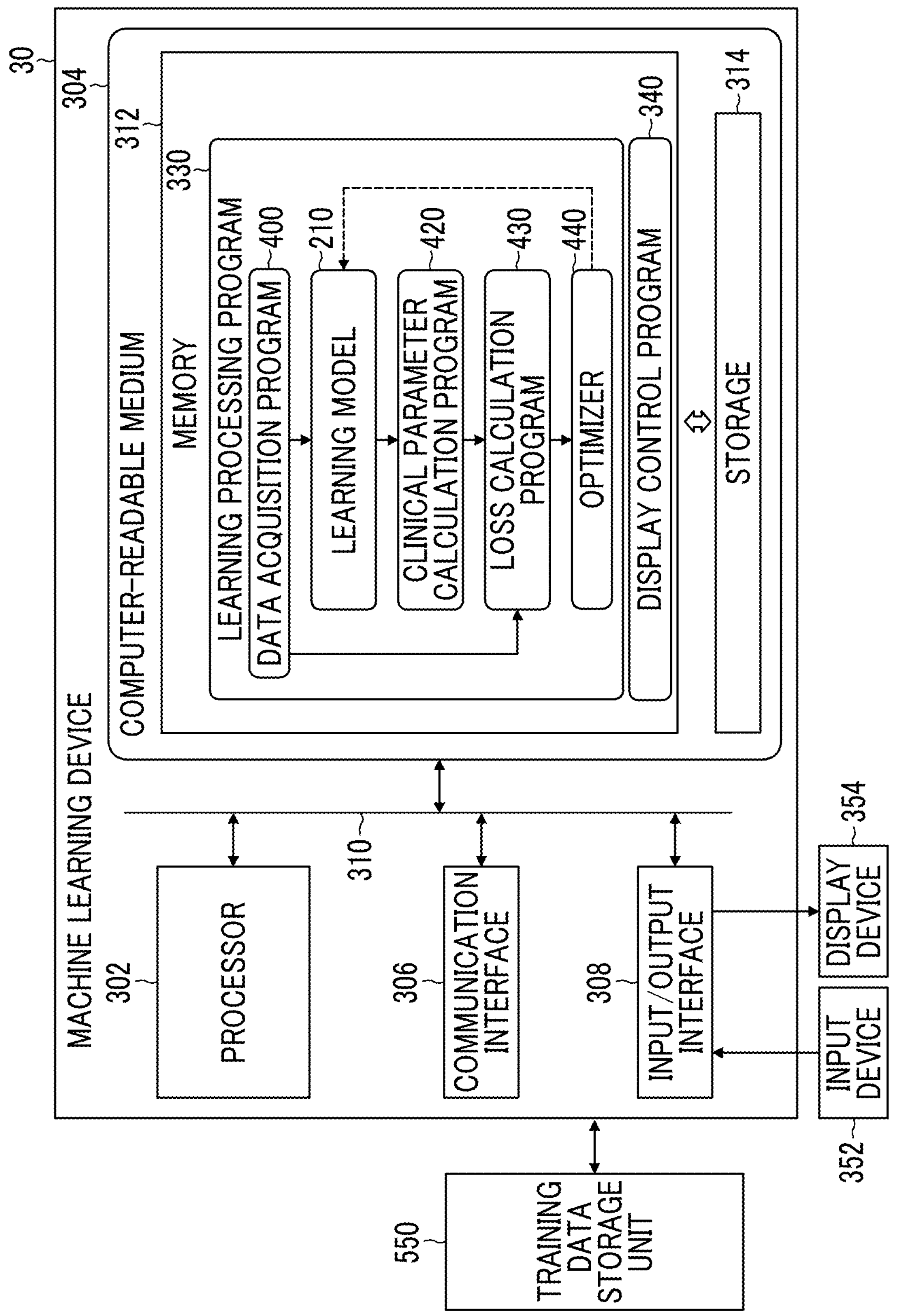
FIG. 9 is a block diagram showing an example of a hardware configuration of the machine learning device applied to the first embodiment.

FIG. 9 is a block diagram showing an example of a hardware configuration of the machine learning device 30. The machine learning device 30 comprises a processor 302, a computer-readable medium 304, which is a non-transitory tangible object, a communication interface 306, an input/output interface 308, and a bus 310. The computer-readable medium 304 includes a memory 312 and a storage 314. The processor 302 is connected to the computer-readable medium 304, the communication interface 306, and the input/output interface 308 via the bus 310. The input device 352 and the display device 354 are connected to the bus 310 via the input/output interface 308. The hardware configuration of the machine learning device 30 may be similar to the corresponding elements of the information processing apparatus 10 described with reference to FIG. 6. A form of the machine learning device 30 may be a server, a personal computer, or a workstation.

The machine learning device 30 is connected to an electric telecommunication line (not shown) via the communication interface 306, and is communicably connected to an external device, such as a training data storage unit 550. The training data storage unit 550 includes a storage in which the training data set including the plurality of training data is stored. It should be noted that the training data storage unit 550 may be built in the storage 314 in the machine learning device 30.

A plurality of programs, data, and the like including a learning processing program 330 and a display control program 340 are stored in the computer-readable medium 304. The learning processing program 330 includes a data acquisition program 400, the learning model 210, a clinical parameter calculation program 420, a loss calculation program 430, and an optimizer 440. The data acquisition program 400 includes an instruction to execute processing of acquiring the training data from the training data storage unit 550. The clinical parameter calculation program 420 may be similar to the clinical parameter calculation program 160 described with reference to FIG. 6.

The loss calculation program 430 includes an instruction to execute processing of calculating a loss indicating an error between the clinical parameter calculated by the clinical parameter calculation program 420 and the correct answer clinical parameter corresponding to the training image. The optimizer 440 includes an instruction to calculate an update amount of the model parameter from the calculated loss, and execute processing of updating the model parameter of the learning model 210.

Generation Method of Training Data

Figure 10:
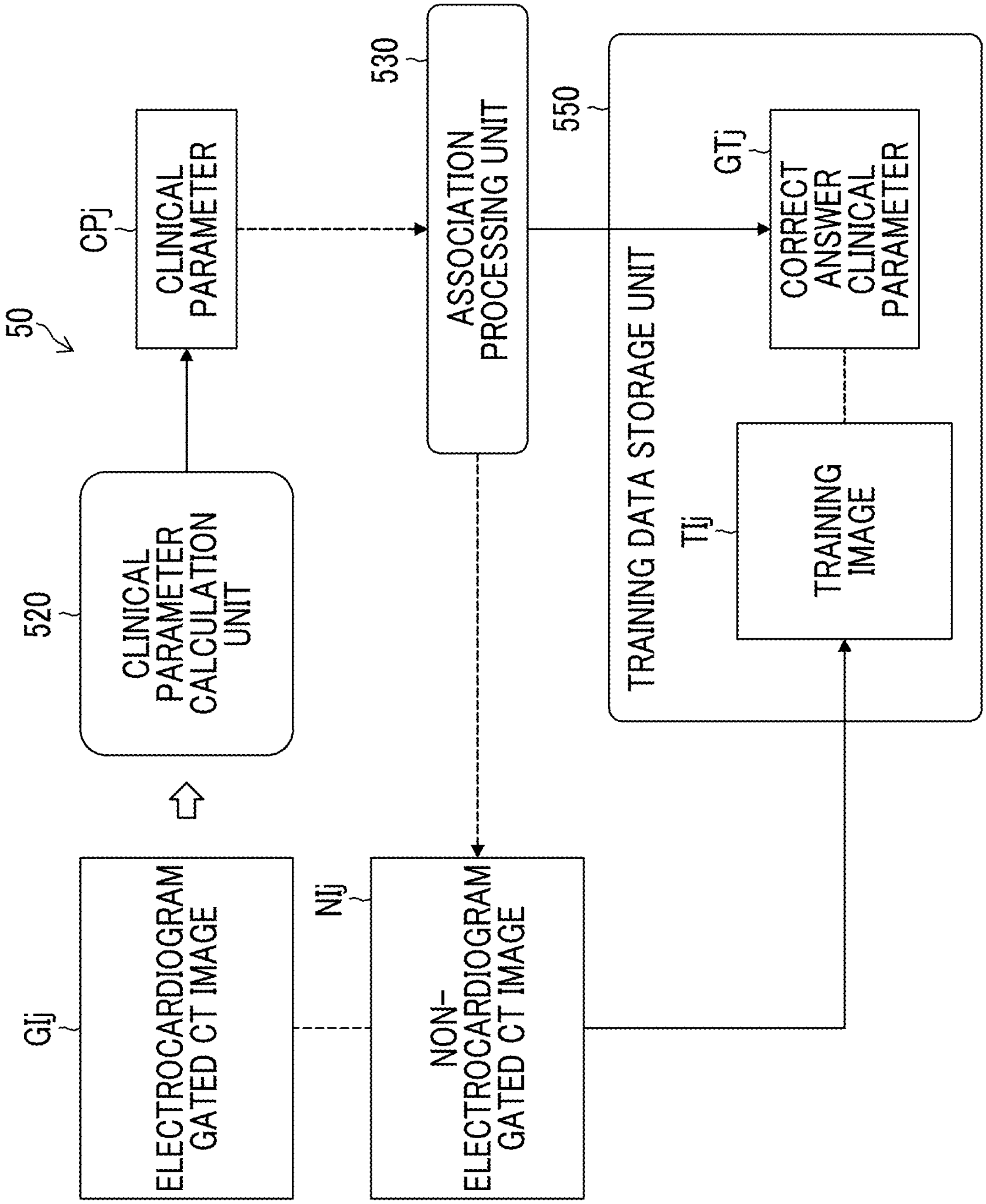
FIG. 10 is a block diagram showing a functional configuration of a training data generation device that performs processing of generating training data used in the machine learning method according to the first embodiment.

FIG. 10 is a block diagram showing a functional configuration of a training data generation device 50 that performs processing of generating the training data used in the machine learning method according to the first embodiment.

The training data generation device 50 includes a clinical parameter calculation unit 520 and an association processing unit 530. In order to generate the training data, first, a plurality of image pairs of a non-electrocardiogram gated CT image NIj and an electrocardiogram gated CT image GIj, which include a region of the same part of the same subject, are prepared.

The non-electrocardiogram gated CT image NIj is the training image TIj for input to the learning model 210. The clinical parameter calculation unit 520 calculates the clinical parameter from the electrocardiogram gated CT image GIj. The association processing unit 530 associates a clinical parameter CPj calculated from the electrocardiogram gated CT image GIj with the non-electrocardiogram gated CT image NIj. That is, the association processing unit 530 associates the clinical parameter CPj calculated from the electrocardiogram gated CT image GIj with the non-electrocardiogram gated CT image NIj as the correct answer clinical parameter GTj corresponding to the non-electrocardiogram gated CT image NIj (training image TIj).

The non-electrocardiogram gated CT image NIj and the clinical parameter CPj, which are associated with each other by the association processing unit 530, are stored in the training data storage unit 550 as the training image TIj and the correct answer clinical parameter GTj. The training data storage unit 550 may be provided in the training data generation device 50, or may be a device different from the training data generation device 50. By performing the similar processing on the image pairs captured for each of the plurality of subjects, the set of the plurality of training data can be obtained. The function of the training data generation device 50 may be incorporated in the machine learning device 30.

FIG. 11 is a conceptual diagram of the training data set stored in the training data storage unit 550. As shown in FIG. 11, the training data set includes a plurality of training data in which the training image TIj for input is associated with a value of the CAC score which is the corresponding correct answer clinical parameter GTj. It is desirable to prepare the training data set as shown in FIG. 11 in advance, acquire a sample from the training data set, and train the learning model 210. It should be noted that it is also possible to generate the training data by calculating the correct answer clinical parameter from the electrocardiogram gated CT image GIj during the training of the learning model 210.

Flowchart of Machine Learning Method Executed by Machine Learning Device 30

Figure 12:
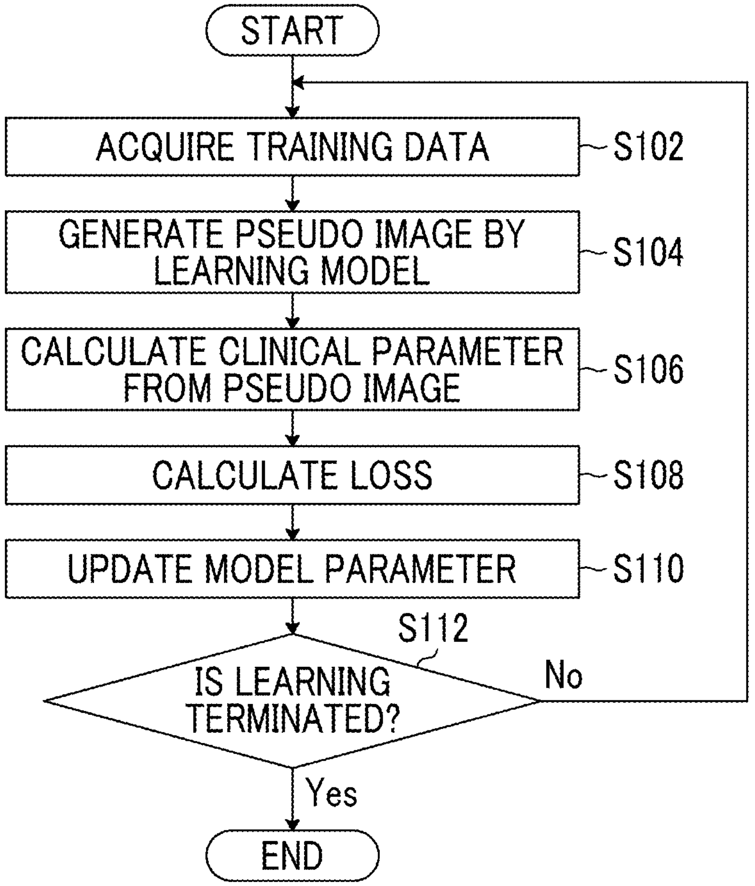
FIG. 12 is a flowchart showing an example of the machine learning method executed by the machine learning device.

FIG. 12 is a flowchart showing an example of a machine learning method executed by the machine learning device 30. In step S102, the processor 302 acquires the training data.

In step S104, the processor 302 inputs the training image TIj of the training data to the learning model 210, and generates the pseudo image by the learning model 210.

In step S106, the processor 302 calculates the clinical parameter from the pseudo image output by the learning model 210.

In step S108, the processor 302 calculates the loss indicating the error between the clinical parameter calculated from the pseudo image and the correct answer clinical parameter GTj associated with the training image TIj.

In step S110, the processor 302 calculates the update amount of the model parameter of the learning model 210 based on the calculated loss, and updates the model parameter. It should be noted that the operations of steps S102 to S110 may be performed in units of mini-batch.

In step S112, the processor 302 determines whether or not to terminate the learning. A termination condition of the learning may be determined based on the value of the loss, or may be determined based on the number of updates of the model parameter. As for a method based on the value of the loss, for example, the termination condition of the learning may include that the loss converges within a prescribed range. Also, as for a method based on the number of updates, for example, the termination condition of the learning may include that the number of updates reaches a prescribed number of times. Alternatively, a data set for performance evaluation of the model may be prepared separately from the training data, and whether or not to terminate the learning may be determined based on the evaluation value using the data for evaluation.

In a case in which a No determination is made in a determination result in step S112, the processor 302 returns to step S102 and continues the learning processing. On the other hand, in a case in which a Yes determination is made in the determination result in step S112, the processor 302 terminates the flowchart of FIG. 12.

The trained learning model 210 trained in this way is incorporated into the information processing apparatus 10 as the image generation model 14. The machine learning method executed by the machine learning device 30 can be understood as the generation method of the image generation model 14, and is an example of a learning model generation method according to the present disclosure.

Flowchart of Information Processing Method Executed by Information Processing Apparatus 10

Figure 13:
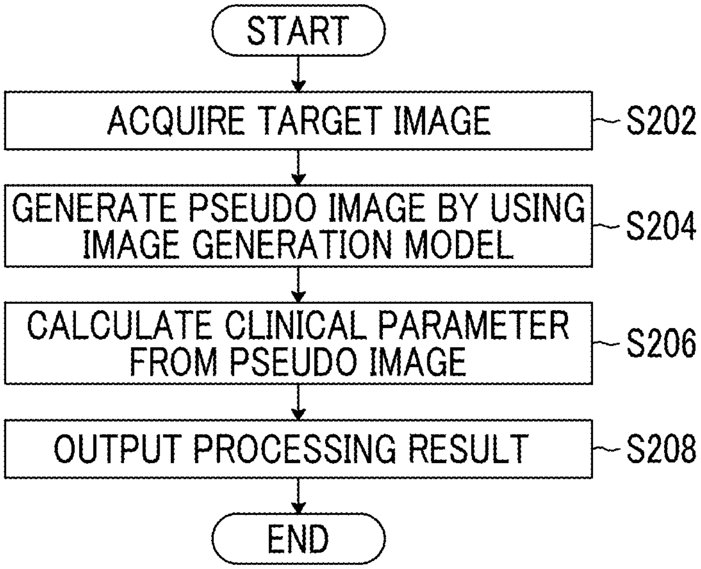
FIG. 13 is a flowchart showing an example of an information processing method executed by the information processing apparatus.

FIG. 13 is a flowchart showing an example of an information processing method executed by the information processing apparatus 10. In step S202, the processor 102 acquires the target image which is the processing target. The target image in this case is the non-electrocardiogram gated CT image. The processor 102 may automatically acquire the target image from an image storage server (not shown) or the like, or may receive the input of the target image via a user interface and acquire a designated image. The image storage server may be, for example, a digital imaging and communications in medicine (DICOM) server.

In step S204, the processor 102 inputs the target image to the image generation model 14, and generates the pseudo image by the image generation model 14.

In step S206, the processor 102 calculates the clinical parameter from the pseudo image.

In step S208, the processor 102 outputs the processing result including the value of the calculated clinical parameter.

After step S208, the processor 102 terminates the flowchart of FIG. 13.

Second Embodiment

In a second embodiment, as an example, a case will be described in which the CAC score is calculated for each perfusion region of the four main branches of the coronary artery.

Configuration of Information Processing Apparatus

Figure 14:
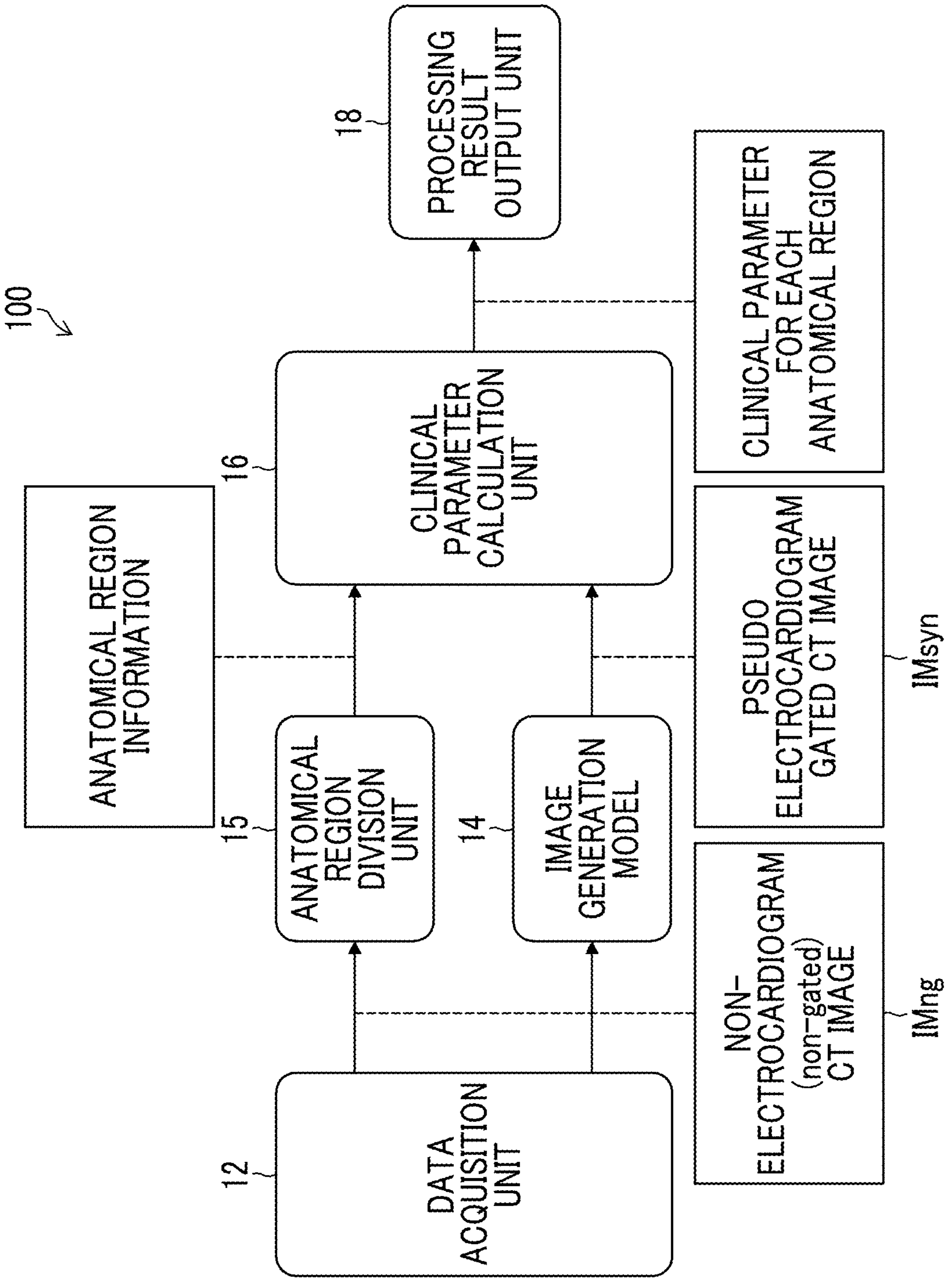
FIG. 14 is a block diagram showing a functional configuration of an information processing apparatus according to a second embodiment.

FIG. 14 is a block diagram showing a functional configuration of an information processing apparatus 100 according to the second embodiment. In FIG. 14, elements having the configurations that are the same as or similar to elements shown in FIG. 5 are designated by the same reference numerals, and the overlapping description thereof will be omitted. A difference of the configuration shown in FIG. 14 from FIG. 5 will be described.

The information processing apparatus 100 shown in FIG. 14 includes an anatomical region division unit 15 that divides the non-electrocardiogram gated CT image input via the data acquisition unit 12 into the perfusion regions of the four main branches of the coronary artery. The perfusion regions of the four main branches of the coronary artery are an example of an anatomical region. The anatomical region division unit 15 is configured by a learning model (segmentation model) trained, through machine learning, for example, to perform segmentation processing of dividing the region of the input image for each of the perfusion regions of the four main branches, and output the region division segmentation result.

Anatomical region information obtained by the anatomical region division unit 15 is transmitted to the clinical parameter calculation unit 16. The clinical parameter calculation unit 16 applies the anatomical region information to the pseudo electrocardiogram gated CT image IMsyn generated by the image generation model 14, and calculates the clinical parameter for each anatomical region. That is, in a case of the second embodiment, the CAC score for each perfusion region of the main branch is calculated. Other configurations may be similar to the configurations described with reference to FIG. 5.

Figure 15:
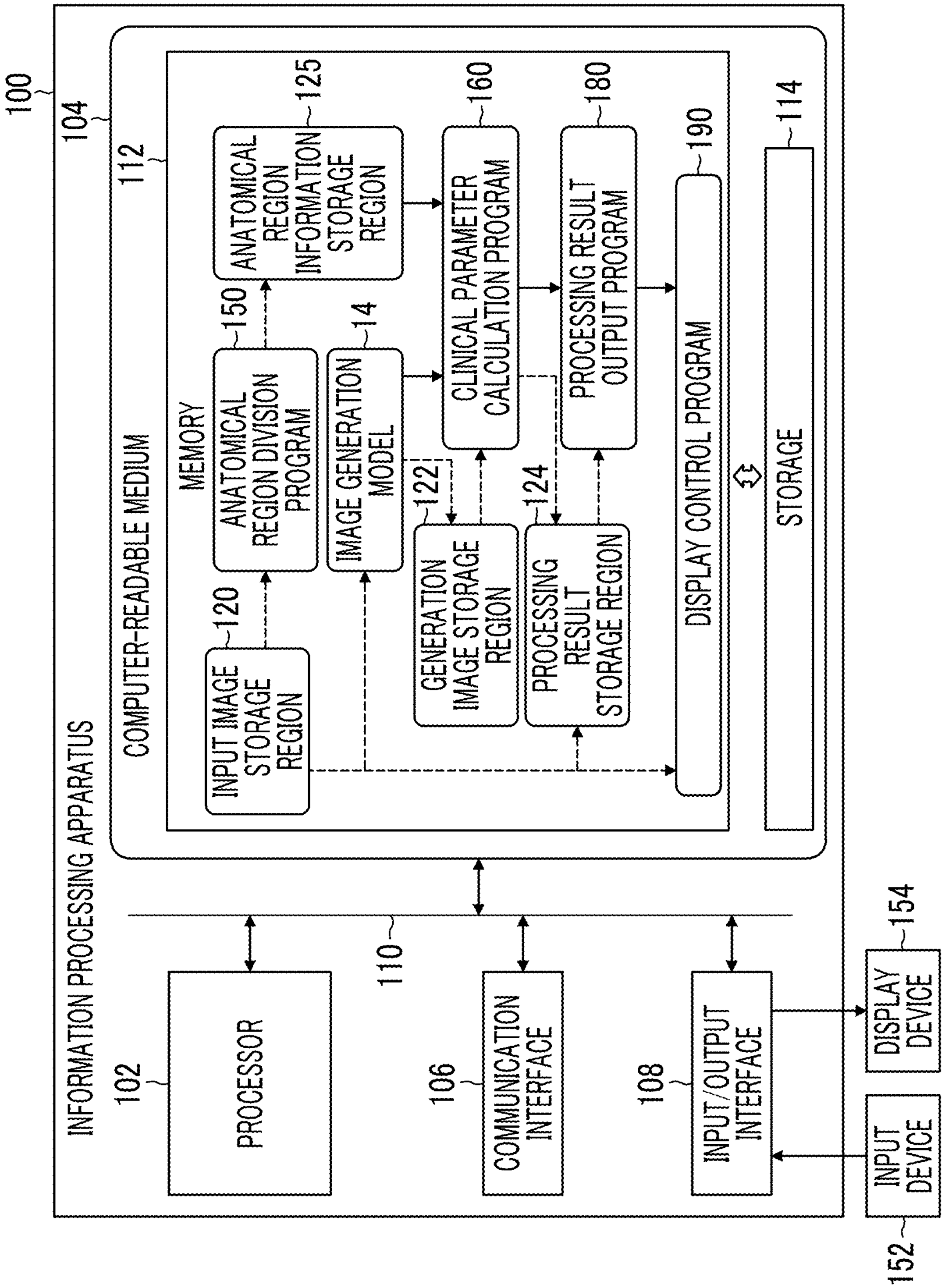
FIG. 15 is a block diagram showing an example of a hardware configuration of the information processing apparatus according to the second embodiment.

FIG. 15 is a block diagram showing an example of a hardware configuration of the information processing apparatus 100 according to the second embodiment. Regarding the configuration shown in FIG. 15, elements having the configurations that are the same as or similar to elements shown in FIG. 6 are designated by the same reference numerals, and the overlapping description thereof will be omitted.

The hardware configuration of the information processing apparatus 100 may be similar to the configuration of the information processing apparatus 10 shown in FIG. 6. In addition to the configuration described with reference to FIG. 6, an anatomical region division program 150 is stored in the computer-readable medium 104 of the information processing apparatus 100. The anatomical region division program 150 may include a trained model trained, through machine learning, to perform the segmentation processing that functions as the anatomical region division unit 15. In addition, the anatomical region division program 150 may an instruction to receive the input of an instruction to designate the anatomical region via the user interface, divide the region of the image based on the instructed information, specify the anatomical region, and generate the anatomical region information.

Moreover, the computer-readable medium 104 of the information processing apparatus 100 includes an anatomical region information storage region 125. The anatomical region information storage region 125 stores the anatomical region information obtained by the anatomical region division program 150. The clinical parameter calculation program 160 applies the anatomical region information to the generation image of the image generation model 14, and calculates the clinical parameter individually for each anatomical region of the generation image. Other configurations may be similar to the configurations described with reference to FIG. 6.

Figure 16:
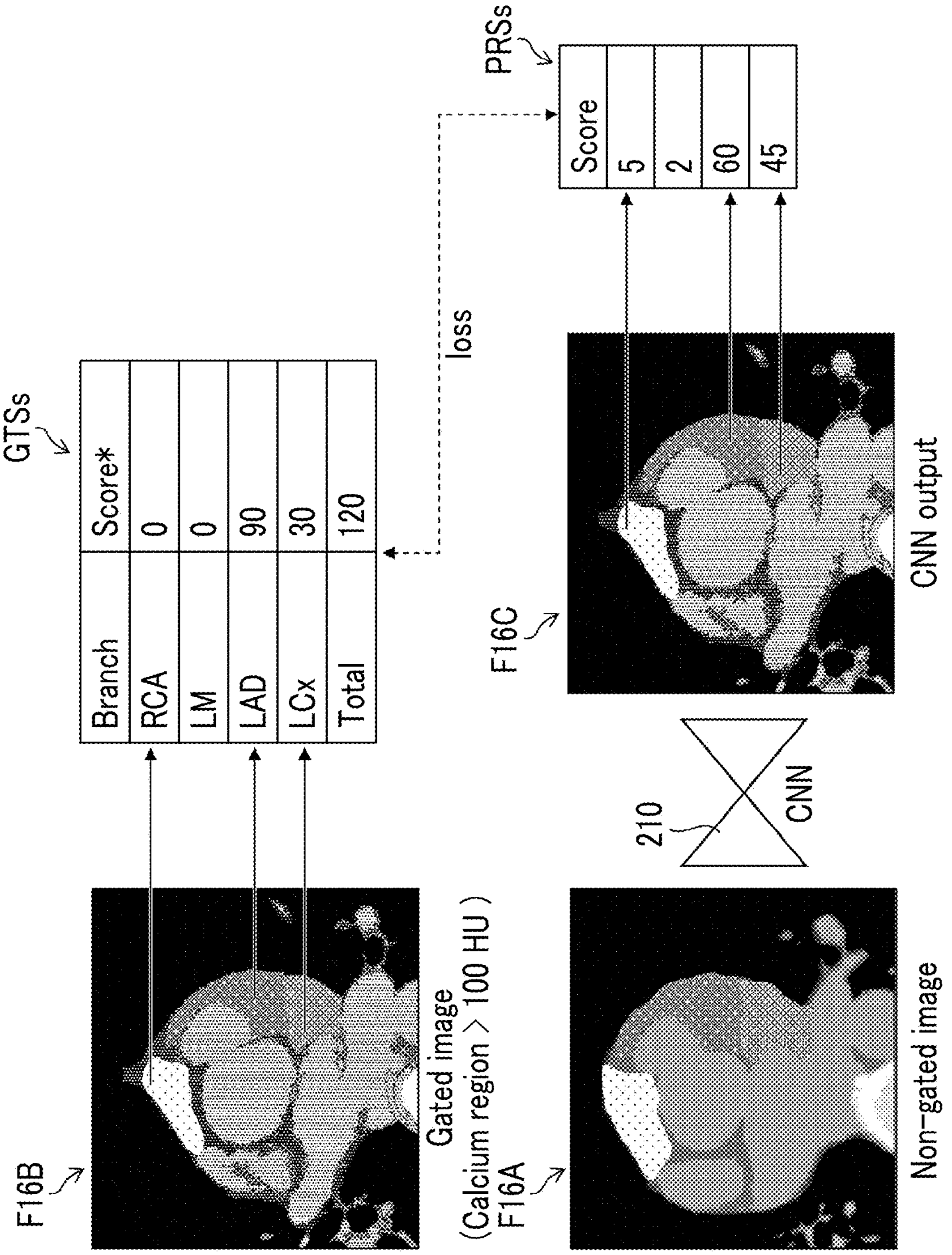
FIG. 16 is an explanatory diagram showing an outline of a machine learning method of generating an image generation model applied to the second embodiment.

FIG. 16 is an explanatory diagram showing an outline of a machine learning method of generating an image generation model 14 applied to the second embodiment. A training data set includes a plurality of training data in which a non-electrocardiogram gated CT image F16A obtained by imaging the subject, information that the perfusion region of each of the four main branches of the coronary artery is divided as the anatomical region information for the non-electrocardiogram gated CT image F16A, and a correct answer CAC score GTSs for each anatomical region calculated from an electrocardiogram gated CT image F16B obtained by imaging the same subject as the non-electrocardiogram gated CT image F16A are associated with each other.

The non-electrocardiogram gated CT image F16A is a training image for input to the learning model 210. The correct answer CAC score GTSs is teacher data corresponding to the non-electrocardiogram gated CT image F16A. The correct answer CAC score GTSs may be, for example, a value obtained by counting the number of voxels in a region in which the CT value is greater than 100 HU for each anatomical region in the electrocardiogram gated CT image F16B. In a case of the second embodiment, the correct answer CAC score GTSs is a set of the CAC scores for each perfusion region of the main branch of the coronary artery. It should be noted that the anatomical region information may be generated from the non-electrocardiogram gated CT image F16A or may be generated from the corresponding electrocardiogram gated CT image F16B.

In this case, the learning model 210 is trained through the following procedures.

[Procedure 1] The non-electrocardiogram gated CT image F16A, which is the training image, is input to the learning model 210.

[Procedure 2] The output of a generation image F16C is obtained from the learning model 210 by inputting the non-electrocardiogram gated CT image F16A.

[Procedure 3] The anatomical region information is applied to the generation image F16C to divide the generation image F16C into the perfusion regions of the coronary artery branches, the generation image F16C is subjected to the threshold value processing under the condition in which the CT value >100 HU, and a CAC score PRSs is calculated individually for each perfusion region. The CAC score PRSs for each region calculated from the generation image F7C is a CAC score predicted from the non-electrocardiogram gated CT image F16A. FIG. 16 shows an example of a case in which the value of the CAC score PRSs for each region corresponding to the four main branches calculated from the generation image F7C is (RCA, LM, LAD, LCx)=(5, 2, 60, 45).

[Procedure 4] A machine learning device including a processor that executes the machine learning calculates a loss from the CAC score PRSs calculated from the generation image F7C and the correct answer CAC score GTSs, and updates a model parameter of the learning model 210 such that the loss is minimized. FIG. 16 shows an example of a case in which the value of the correct answer CAC score GTSs for each region corresponding to the four main branches is (RCA, LM, LAD, LCx)=(0,0,90,30). In the learning model 210, the model parameter is updated such that the value of each clinical parameter calculated from the generation image F7C for each anatomical region approaches the value of the correct answer clinical parameter of the corresponding anatomical region.

By repeating the above procedures 1 to 4 using the plurality of training data, the model parameter of the learning model 210 is optimized, and the learning model 210 is trained to generate the generation image F16C in which the CAC score PRSs is calculated with the same level of accuracy as the correct answer CAC score GTSs.

Figure 17:
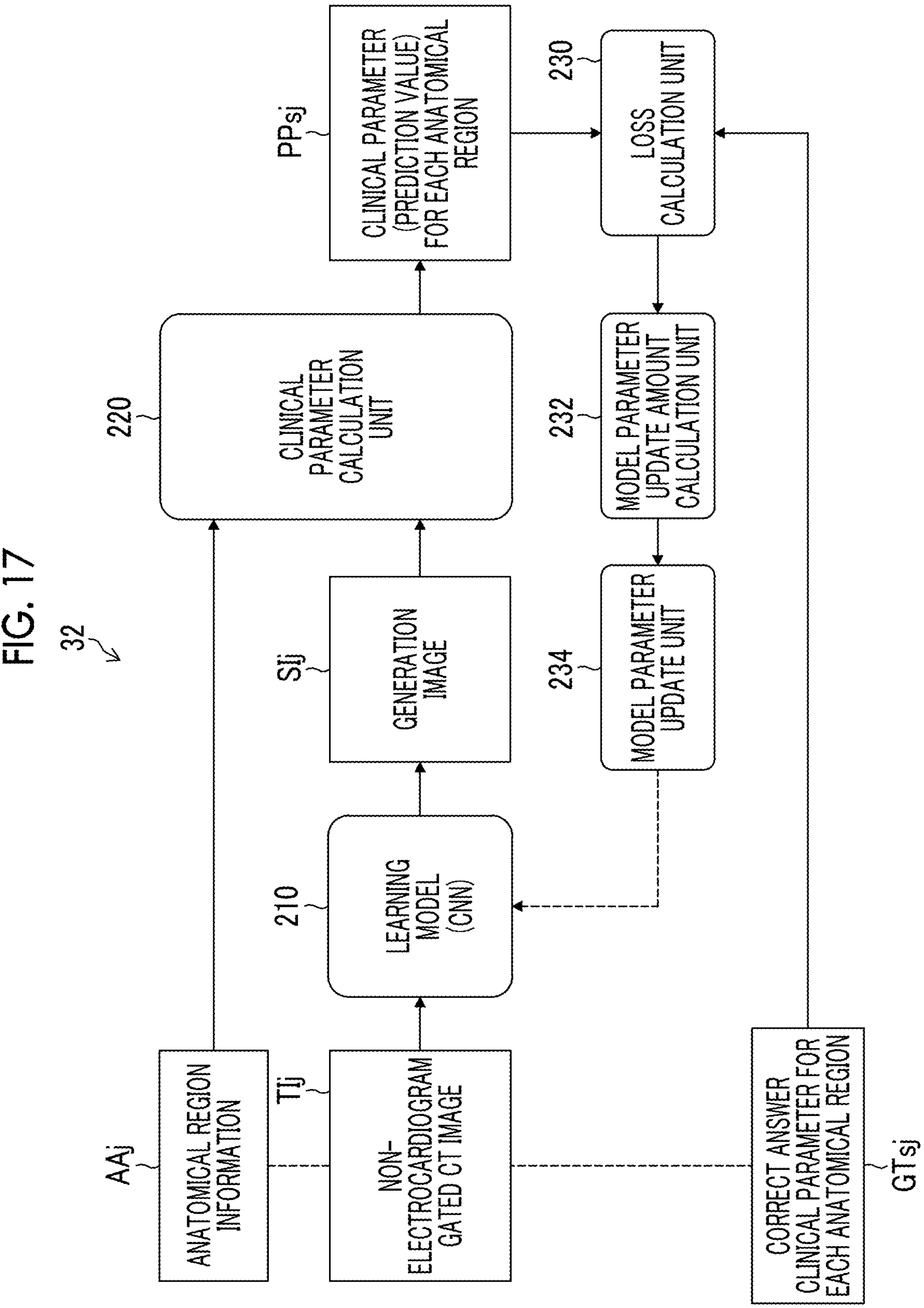
FIG. 17 is a block diagram showing a functional configuration of a machine learning device applied to the second embodiment.

FIG. 17 is a block diagram showing a functional configuration of a machine learning device 32 applied to the second embodiment. Regarding the configuration shown in FIG. 17, elements having the configurations that are the same as or similar to elements shown in FIG. 8 are designated by the same reference numerals, and the overlapping description thereof will be omitted.

The training data acquired by the machine learning device 32 includes anatomical region information AAj for the training image TIj which is the non-electrocardiogram gated CT image. In addition, the correct answer clinical parameter associated with the training image TIj is a correct answer clinical parameter GTsj for each anatomical region.

The clinical parameter calculation unit 220 calculates a clinical parameter PPsj for each anatomical region based on the generation image SIj output from the learning model 210 and the anatomical region information AAj. Other configurations may be similar to the configurations described with reference to FIG. 8.

Figure 18:
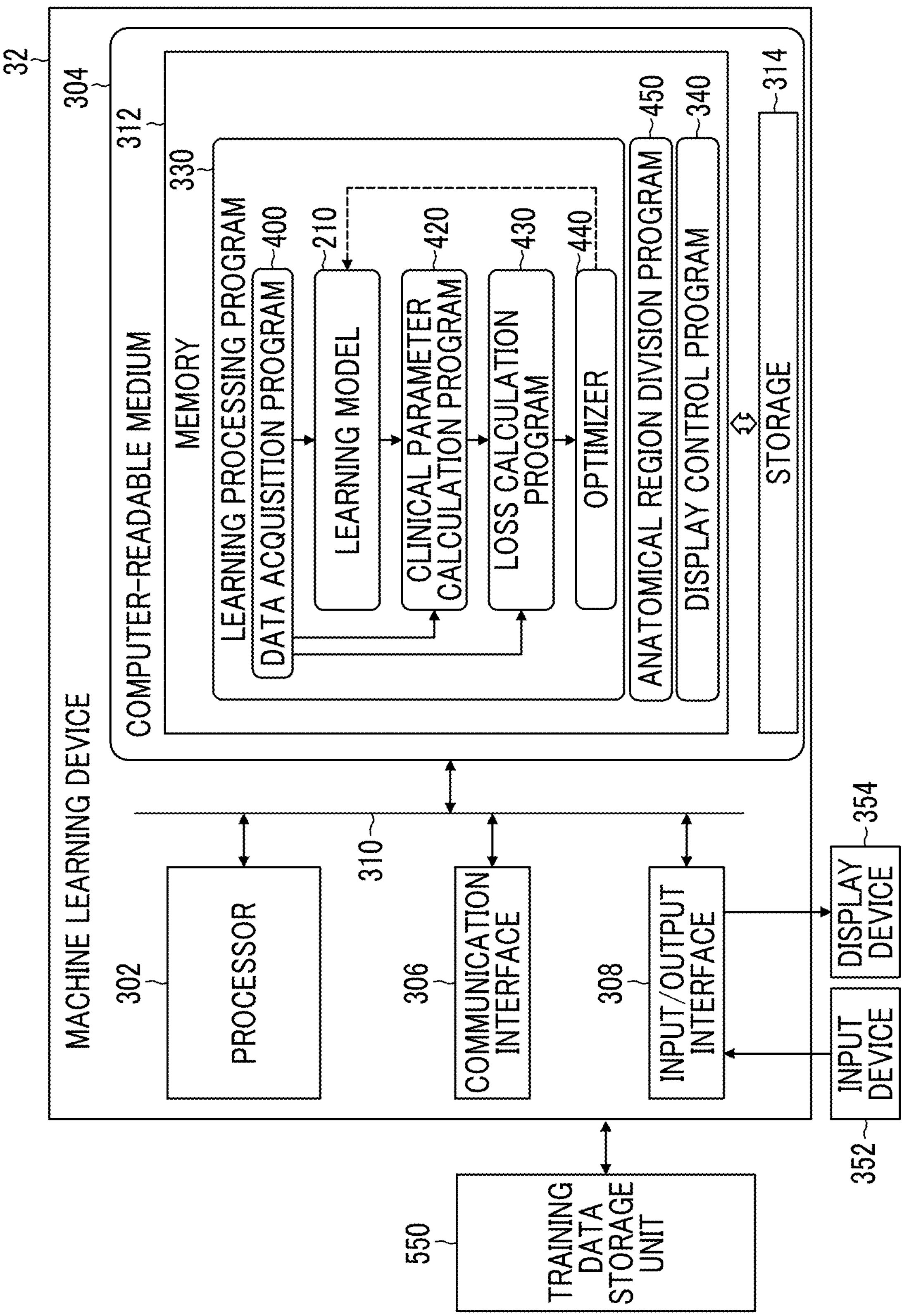
FIG. 18 is a block diagram showing an example of a hardware configuration of the machine learning device applied to the second embodiment.

FIG. 18 is a block diagram showing an example of a hardware configuration of the machine learning device 32 applied to the second embodiment. Regarding the configuration shown in FIG. 18, elements having the configurations that are the same as or similar to elements shown in FIG. 9 are designated by the same reference numerals, and the overlapping description thereof will be omitted.

The hardware configuration of the machine learning device 32 may be similar to the configuration shown in FIG. 9. In addition to the configuration described with reference to FIG. 9, an anatomical region division program 450 is stored in the computer-readable medium 304. The anatomical region division program 450 may have the similar configuration to the anatomical region division program 150 described with reference to FIG. 15.

The training data storage unit 550 stores a training data set including a plurality of training data in which the training image TIj, the anatomical region information AAj for the training image TIj, the correct answer clinical parameter GTsj for each anatomical region are associated with each other.

The data acquisition program 400 includes an instruction to execute processing of acquiring the training data including the anatomical region information AAj. The clinical parameter calculation program 420 includes an instruction to execute processing of calculating the clinical parameter for each anatomical region from the generation image SIj based on the anatomical region information AAj and the generation image SIj. In addition, the loss calculation program 430 includes an instruction to execute processing of calculating a loss from the clinical parameter PPsj for each anatomical region calculated from the generation image SIj and the correct answer clinical parameter GTsj for each anatomical region associated with the training image TIj. Other configurations may be similar to the configurations described with reference to FIG. 9.

Figure 19:
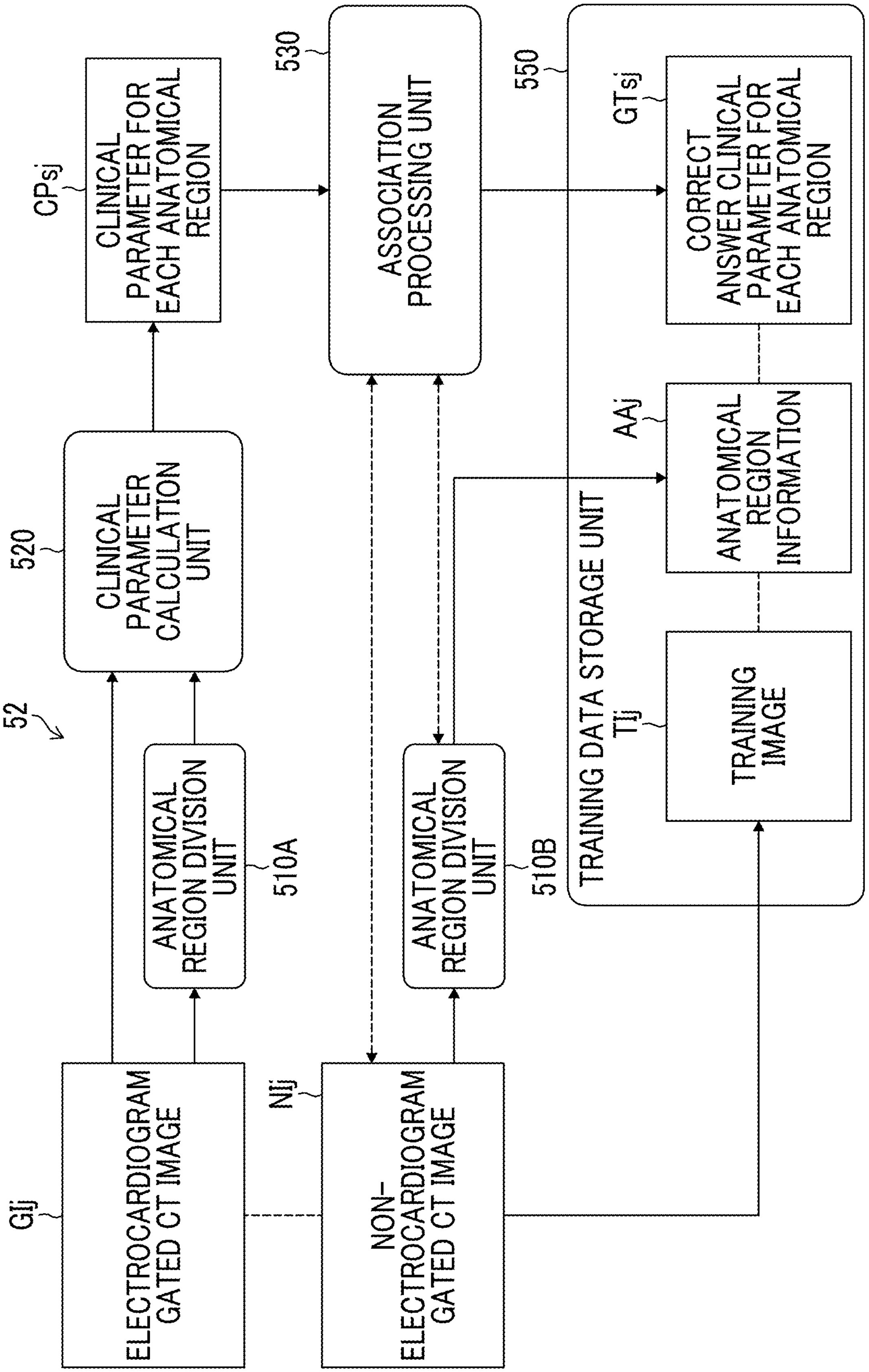
FIG. 19 is a block diagram showing a functional configuration of a training data generation device that performs processing of generating training data used in the machine learning method according to the second embodiment.

FIG. 19 is a block diagram showing a functional configuration of a training data generation device 52 that performs processing of generating the training data used in the machine learning method according to the second embodiment. In FIG. 19, elements having the configurations that are the same as or similar to elements shown in FIG. 10 are designated by the same reference numerals, and the overlapping description thereof will be omitted.

The training data generation device 52 has a configuration in which anatomical region division units 510A and 510B are added to the configuration shown in FIG. 10. It should be noted that, although the anatomical region division units 510A and 510B are shown in FIG. 19, the anatomical region division units 510A and 510B may be a common (single) processing unit. In addition, although FIG. 19 shows an example in which the anatomical region information is acquired from each of the electrocardiogram gated CT image GIj and the non-electrocardiogram gated CT image NIj, since the anatomical region information obtained from the non-electrocardiogram gated CT image NIj by the anatomical region division unit 510B has substantially the same level of accuracy as the anatomical region information obtained from the electrocardiogram gated CT image GIj, a configuration may be adopted in which the anatomical region information is acquired from only one image.

For example, the anatomical region information obtained from the electrocardiogram gated CT image GIj may be associated with the training image TIj and used as the anatomical region information AAj of the training data. Alternatively, a clinical parameter CPsj for each anatomical region may be calculated by applying the anatomical region information AAj obtained from the non-electrocardiogram gated CT image NIj to the clinical parameter calculation unit 520.

Flowchart of Machine Learning Method Executed by Machine Learning Device 32

Figure 20:
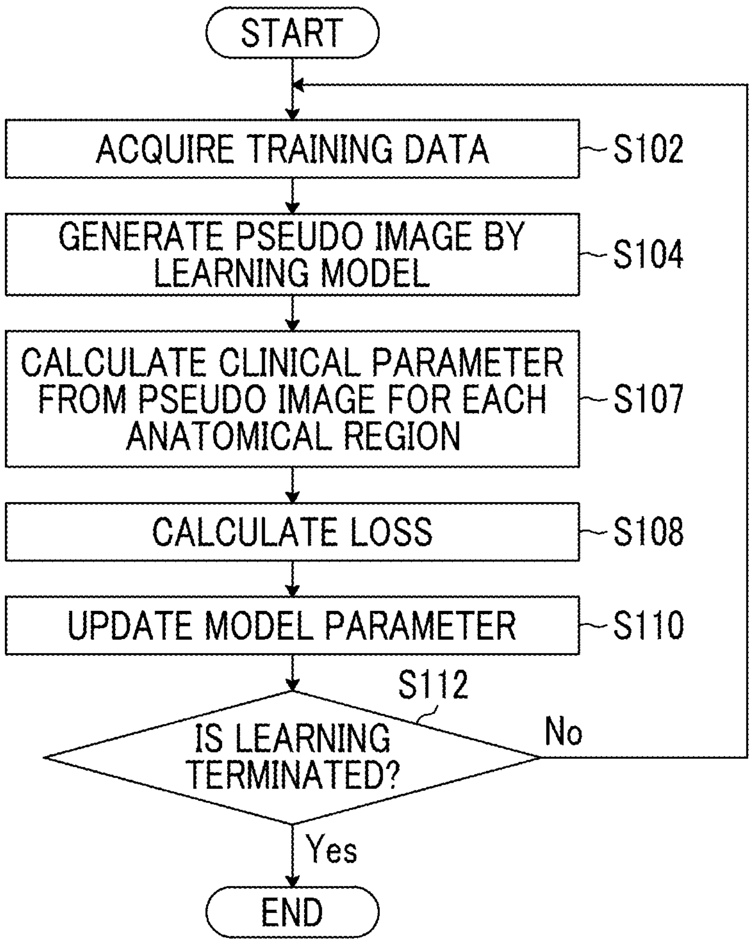
FIG. 20 is a flowchart showing an example of the machine learning method executed by the machine learning device applied to the second embodiment.

FIG. 20 is a flowchart showing an example of a machine learning method executed by the machine learning device 32. Regarding the flowchart shown in FIG. 20, the steps common to steps in FIG. 12 are designated by the same step numbers, and the overlapping description will be omitted.

The flowchart shown in FIG. 20 includes step S107 instead of step S106 of FIG. 12. After step S104, in step S107, the processor 302 calculates the clinical parameter PPsj for each anatomical region from the pseudo image based on the pseudo image (generation image SIj) generated by the learning model and the anatomical region information AAj associated with the training image TIj.

In step S108, the processor 302 calculates a loss from the clinical parameter PPsj for each anatomical region calculated from the pseudo image and the correct answer clinical parameter GTsj for each anatomical region associated with the training image TIj.

Other steps may be similar to steps in the flowchart of FIG. 12. The trained learning model 210 trained in this way is incorporated into the information processing apparatus 100 as the image generation model 14.

Flowchart of Information Processing Method Executed by Information Processing Apparatus 100

Figure 21:
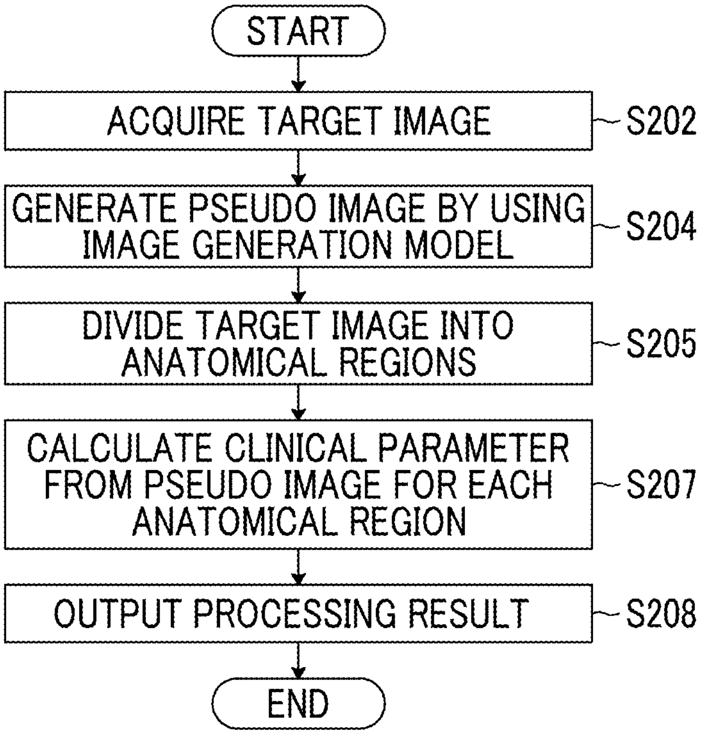
FIG. 21 is a flowchart showing an example of an information processing method executed by the information processing apparatus according to the second embodiment.

FIG. 21 is a flowchart showing an example of an information processing method executed by the information processing apparatus 100 according to the second embodiment. Regarding the flowchart shown in FIG. 21, the steps common to steps in FIG. 13 are designated by the same step numbers, and the overlapping description will be omitted.

The flowchart shown in FIG. 21 includes steps S205 and S207 instead of step S206 of FIG. 13.

After step S204, the processor 102 divides the target image into the anatomical regions, and acquires the anatomical region information.

In step S207, the processor 102 calculates the clinical parameter for each anatomical region from the pseudo image based on the pseudo image generated by the image generation model 14 and the anatomical region information. In a case of the second embodiment, the CAC score for each perfusion region of the four main branches of the coronary artery is calculated. Other steps may be similar to steps in the flowchart of FIG. 13.

Figure 22:
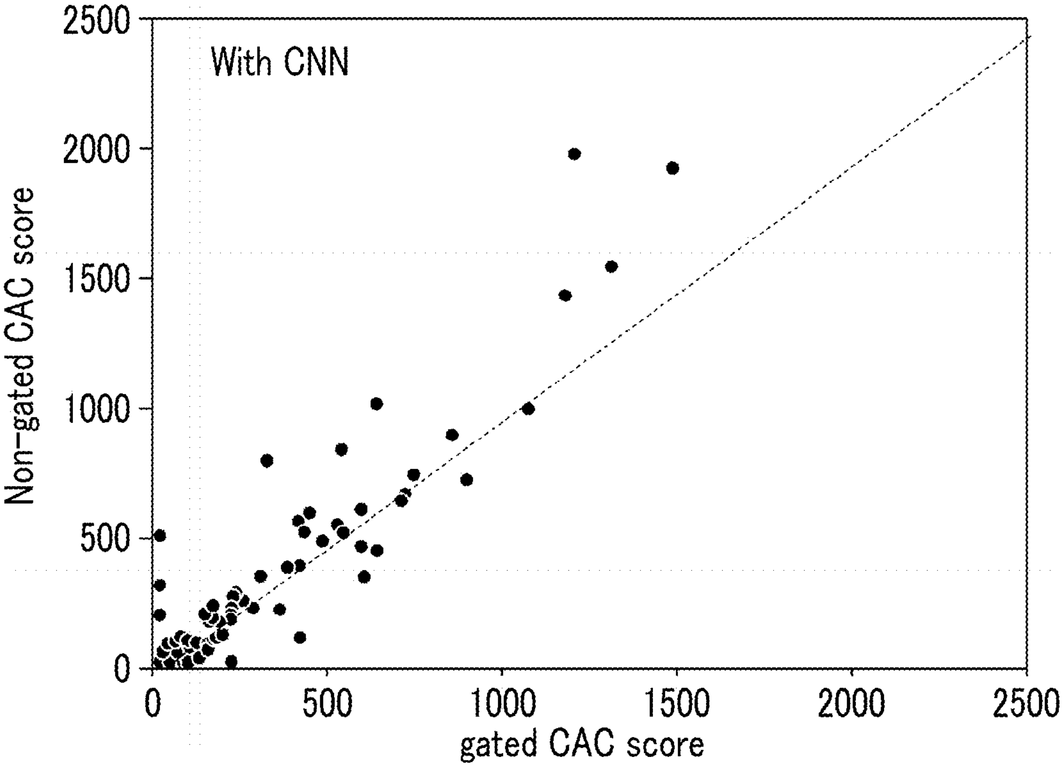
FIG. 22 is a graph showing a relationship between a CAC score calculated from a non-electrocardiogram gated CT image by using the information processing apparatus according to the second embodiment and a CAC score calculated from an electrocardiogram gated CT image.

Verification of Accuracy of CAC Scoring Based on Non-Electrocardiogram Gated CT Image FIG. 22 is a graph showing a relationship between the CAC score calculated from the non-electrocardiogram gated CT image by using the information processing apparatus 100 according to the second embodiment and the CAC score calculated from the electrocardiogram gated CT image corresponding to the same subject. As shown in FIG. 22, both the CAC scores substantially match.

Figure 23:
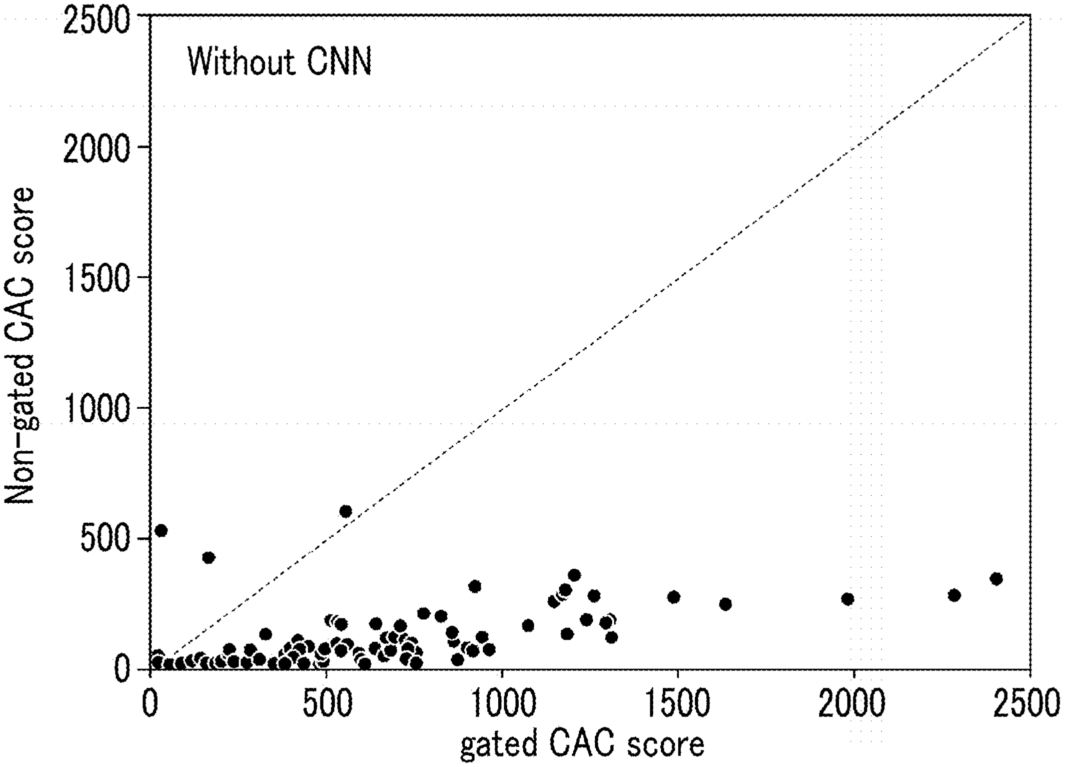
FIG. 23 is a graph showing a relationship between a CAC score calculated from a non-electrocardiogram gated CT image by using an information processing apparatus according to a comparative example and a CAC score calculated from an electrocardiogram gated CT image.

FIG. 23 is a graph showing a relationship between the CAC score calculated from the non-electrocardiogram gated CT image by using an information processing apparatus according to a comparative example and the CAC score calculated from the electrocardiogram gated CT image. The information processing apparatus according to the comparative example is configured to calculate the CAC score by performing the threshold value processing on the non-electrocardiogram gated CT image without using the image generation model 14. In this case, as shown in FIG. 23, both the CAC scores are significantly different from each other.

Figure 24:
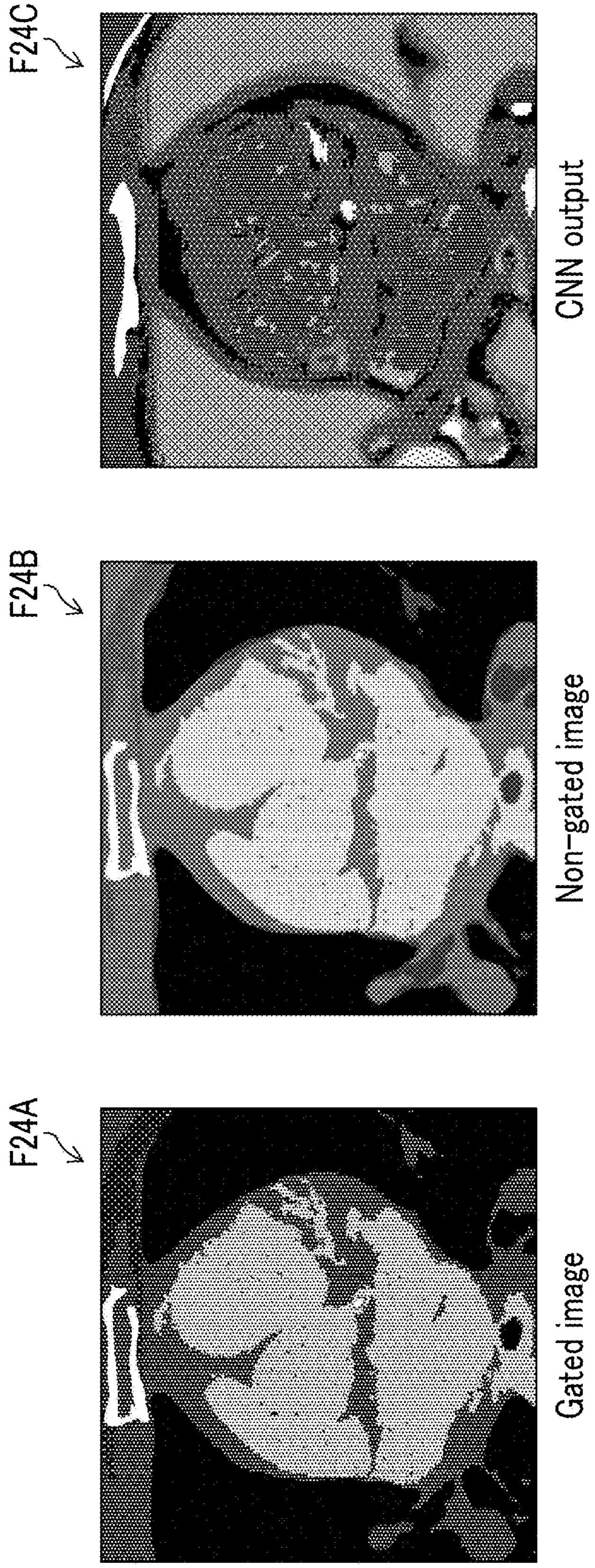
FIG. 24 is an image example of each of the electrocardiogram gated CT image, the non-electrocardiogram gated CT image, and a pseudo image generated from the non-electrocardiogram gated CT image used in the calculation of the CAC score.

FIG. 24 shows an example of an image used for the CAC scoring shown in FIGS. 22 and 23. A left figure F24A of FIG. 24 is an example of the electrocardiogram gated CT image. A central figure F24B is an example of the non-electrocardiogram gated CT image of the same subject as the left figure F24A. A right figure F24C is an example of the pseudo image generated by the image generation model 14 from the non-electrocardiogram gated CT image of the central figure F24B. As is clear from a comparison between the left figure F24A and the right figure F24C, the pseudo image output by the image generation model 14 can be an image having appearance features different from the electrocardiogram gated CT image of the real image.

Program Causing Computer to Operate

A program causing the computer to realize a part or all of the processing functions in each device of the information processing apparatus 10, the machine learning device 30, and the training data generation device 50 according to the first embodiment, and the information processing apparatus 100, the machine learning device 32, and the training data generation device 52 according to the second embodiment can be recorded in a computer-readable medium that is a non-transitory information storage medium, such as an optical disk, a magnetic disk, a semiconductor memory, or other tangible objects, and the program can be provided via the information storage medium.

Also, instead of the aspect in which the program is stored in such a tangible non-transitory computer-readable medium and provided, a program signal can be provided as a download service by using an electric telecommunication line, such as the Internet.

Further, a part or all of the processing functions in each of the devices described above may be realized by cloud computing, or can be provided as software as a service (SaaS).

Hardware Configuration of Each Processing Unit

The hardware structure of processing units that execute various types of processing, such as the data acquisition unit 12, the image generation unit including the image generation model 14, the anatomical region division unit 15, the clinical parameter calculation unit 16, and the processing result output unit 18 in the information processing apparatus 10 and the information processing apparatus 100, the image generation unit including the learning model 210, the clinical parameter calculation unit 220, the loss calculation unit 230, the model parameter update amount calculation unit 232, and the model parameter update unit 234 in the machine learning device 30 and the machine learning device 32, and the anatomical region division units 510A and 510B, the clinical parameter calculation unit 520, and the association processing unit 530 in the training data generation device 50 and the training data generation device 52, is various processors shown below, for example.

The various processors include a CPU that is a general-purpose processor executing the program and functioning as the various processing units, a GPU, a programmable logic device (PLD) that is a processor of which a circuit configuration can be changed after manufacture, such as a field programmable gate array (FPGA), and a dedicated electric circuit that is a processor having a circuit configuration that is designed for exclusive use in order to execute specific processing, such as an application specific integrated circuit (ASIC).

One processing unit may be configured by one of these various processors or may be configured by two or more processors of the same type or different types. For example, one processing unit may be configured by a plurality of FPGAs, a combination of a CPU and an FPGA, or a combination of a CPU and a GPU. In addition, a plurality of the processing units may be configured by one processor. As an example in which the plurality of processing units are configured by one processor, first, there is a form in which one processor is configured by a combination of one or more CPUs and software, and this processor functions as the plurality of processing units, as represented by a computer, such as a client or a server. Second, there is a form in which a processor, which realizes the functions of the entire system including the plurality of processing units with one integrated circuit (IC) chip, is used, as represented by a system on chip (SoC) or the like. As described above, various processing units are configured by one or more of the various processors described above, as the hardware structure.

Further, the hardware structure of these various processors is, more specifically, an electric circuit (circuitry) in which circuit elements, such as semiconductor elements, are combined.

Advantages of First Embodiment and Second Embodiment

With the information processing apparatus 10 according to the first embodiment and the information processing apparatus 100 according to the second embodiment described above, the following effects can be obtained.

[1] It is possible to calculate the CAC score from the non-electrocardiogram gated CT image with the same level of accuracy as the electrocardiogram gated CT image.

[2] The non-electrocardiogram gated CT image can be acquired by a simpler imaging method than the electrocardiogram gated CT image, and can be acquired by using a normal CT apparatus without requiring a particularly expensive high-performance imaging system.

[3] The non-electrocardiogram gated CT image has a smaller radiation dose to the subject than the electrocardiogram gated CT image, and can be acquired with a low load on the subject.

[4] The CAC score calculated by each of the information processing apparatus 10 and the information processing apparatus 100 can be described by the calculation process, and a logical satisfaction feeling can be obtained about the value of the calculation result.

Other Clinical Parameters

In each of the embodiments described above, the example has been described in which the CAC score is calculated as the clinical parameter, but the clinical parameter is not limited to the CAC score and may be a CAC severity stage indicating the severity of the calcification. In addition, the clinical parameter may be a cardiovascular calcium volume or an Agatston score.

Type of Medical Image

In the technology of the present disclosure, in addition to the CT image, various medical images captured by various medical devices (modalities), such as an MR image captured by using a magnetic resonance imaging (MRI) apparatus, an ultrasound image that projects human body information, a PET image captured by using a positron emission tomography (PET) apparatus, and an endoscopic image captured by using an endoscope apparatus, can be targeted. The image targeted by the technology of the present disclosure is not limited to the three-dimensional image, and may be a two-dimensional image. It should be noted that, in a case of a configuration in which the two-dimensional image is handled, the "voxel" in the contents described in each of the embodiments described above is replaced with a "pixel" and applied.

Others

The present disclosure is not limited to the embodiments described above, and various modifications can be made without departing from the spirit of the technical idea of the present disclosure.

EXPLANATION OF REFERENCES

10, 100: information processing apparatus
12: data acquisition unit
14: image generation model
15: anatomical region division unit
16: clinical parameter calculation unit
18: processing result output unit
30, 32: machine learning device
50, 52: training data generation device
102: processor
104: computer-readable medium
106: communication interface
108: input/output interface
110: bus
112: memory
114: storage
120: input image storage region
122: generation image storage region
124: processing result storage region
125: anatomical region information storage region
150: anatomical region division program
152: input device
154: display device
160: clinical parameter calculation program
180: processing result output program
190: display control program
210: learning model
220: clinical parameter calculation unit
230: loss calculation unit
232: model parameter update amount calculation unit
234: model parameter update unit
302: processor
304: computer-readable medium
306: communication interface
308: input/output interface
310: bus
314: storage
330: learning processing program
340: display control program
352: input device
354: display device
400: data acquisition program
420: clinical parameter calculation program
430: loss calculation program
440: optimizer
450: anatomical region division program
510A: anatomical region division unit
510B: anatomical region division unit
520: clinical parameter calculation unit
530: association processing unit
550: training data storage unit
AAj: anatomical region information
CPj: clinical parameter
CPsj: clinical parameter
F1A: left figure
F1B: right figure
F2A: image
F2B: image
F3A: electrocardiogram gated CT image
F4A: non-electrocardiogram gated CT image
F7A: non-electrocardiogram gated CT image F7B: electrocardiogram gated CT image
F7C: generation image
F16A: non-electrocardiogram gated CT image
F16B: electrocardiogram gated CT image
F16C: generation image
F24A: left figure
F24B: central figure
F24C: right figure
GIj: electrocardiogram gated CT image
GTj: correct answer clinical parameter
GTS: CAC score
GTsj: correct answer clinical parameter
GTSs: correct answer CAC score
IMng: non-electrocardiogram gated CT image
IMsyn: pseudo electrocardiogram gated CT image
NIj: non-electrocardiogram gated CT image
PPj: clinical parameter
PPsj: clinical parameter
PRS: CAC score
PRSs: CAC score
SIj: generation image
TIj: training image
S102 to S112: steps of machine learning method
S202 to S208: steps of information processing method

What is claimed is:

1. An information processing apparatus comprising:
one or more processors; and
one or more storage devices that store a program to be executed by the one or more processors,
wherein the program includes an image generation model trained to generate, from a first image which is input, a second image that imitates an image obtained by an imaging protocol different from an imaging protocol of the first image,
the image generation model is a model trained, through machine learning using a plurality of training data,
wherein the plurality of training data comprises a training image captured by a first imaging protocol for a designated subject using a designated type of modality and a correct answer clinical parameter calculated from a corresponding image captured by a second imaging protocol different from the first imaging protocol for the designated subject using the designated type of modality, such that a clinical parameter calculated from a generation image output by the image generation model in response to input of the training image approaches the correct answer clinical parameter, and
wherein the one or more processors
input the first image captured by the first imaging protocol to the image generation model,
receive the second image output by the image generation model, and
calculate the clinical parameter from the second image.

2. The information processing apparatus according to claim 1,
wherein the one or more processors
divide the first image into anatomical regions, and
calculate the clinical parameter for each of the divided anatomical regions.

3. The information processing apparatus according to claim 2,
wherein each of the training image and the corresponding image is divided into the anatomical regions, and the correct answer clinical parameter is calculated for each of the divided anatomical regions of the corresponding image, and
the image generation model is a model trained such that each clinical parameter calculated from the generation image for each of the divided anatomical regions of the training image approaches the correct answer clinical parameter of each of the divided anatomical regions of the corresponding image.

4. The information processing apparatus according to claim 2,
wherein the divided anatomical region is a perfusion region of a coronary artery.

5. The information processing apparatus according to claim 2,
wherein the clinical parameter is a calcium volume for each main branch of a coronary artery.

6. The information processing apparatus according to claim 1,
wherein the first image is a non-electrocardiogram gated CT image captured by non-electrocardiogram gated imaging, and
the second image is an image that imitates an electrocardiogram gated CT image obtained by electrocardiogram gated imaging.

7. The information processing apparatus according to claim 1,
wherein the training image is captured under a condition of a lower dose than the corresponding image.

8. The information processing apparatus according to claim 1,
wherein the first imaging protocol has a lower dose than the second imaging protocol.

9. The information processing apparatus according to claim 1,
wherein the first imaging protocol has a slower scan speed than the second imaging protocol.

10. The information processing apparatus according to claim 1,
wherein the clinical parameter is a calcification score.

11. The information processing apparatus according to claim 1,
wherein the clinical parameter is a cardiovascular calcium volume.

12. The information processing apparatus according to claim 1,
wherein the clinical parameter is severity of coronary artery calcification.

13. The information processing apparatus according to claim 1,
wherein the image generation model is configured by a neural network.

14. An information processing method executed by one or more processors, the method comprising:
via the one or more processors,
acquiring a first image captured by a first imaging protocol for a designated subject using a designated type of modality;
inputting the first image to an image generation model and receiving a second image, that imitates an image obtained in a case in which imaging is performed by a second imaging protocol different from the first imaging protocol for the designated subject using the designated type of modality, output by the image generation model; and
calculating a clinical parameter from the second image,
wherein the image generation model is a model trained, by using a plurality of training data,
wherein the plurality of training data comprises a training image captured by the first imaging protocol and a correct answer clinical parameter calculated from a corresponding image captured by the second imaging protocol for the designated subject using the designated type of modality, such that the clinical parameter calculated from a generation image output by the image generation model in response to input of the training image approaches the correct answer clinical parameter.

15. A non-transitory, computer-readable tangible recording medium which records thereon a program for causing, when read by a computer, the computer to realize:

a function of acquiring a first image captured by a first imaging protocol for a designated subject using a designated type of modality;

a function of inputting the first image to an image generation model and receiving a second image, that imitates an image obtained in a case in which imaging is performed by a second imaging protocol different from the first imaging protocol for the designated subject using the designated type of modality, output by the image generation model; and a function of calculating a clinical parameter from the second image, wherein the image generation model is a model trained, through machine learning using a plurality of training data, wherein the plurality of training data comprises a training image captured by the first imaging protocol and a correct answer clinical parameter calculated from a corresponding image captured by the second imaging protocol for the designated subject using the designated type of modality, such that the clinical parameter calculated from a generation image output by the image generation model in response to input of the training image approaches the correct answer clinical parameter.

16. A learning model generation method of generating a learning model that enables a computer to realize a function of generating, from an image which is input, a pseudo image that imitates an image obtained by an imaging protocol different from an imaging protocol of the image, the method comprising:

via a system including one or more processors, performing machine learning using a plurality of training data comprising a training image captured by a first imaging protocol for a designated subject using a designated type of modality and a correct answer clinical parameter calculated from a corresponding image captured by a second imaging protocol different from the first imaging protocol for the designated subject using the designated type of modality; and inputting the training image to the learning model, calculating a clinical parameter from a generation image output by the learning model, and training the learning model such that the clinical parameter calculated from the generation image approaches the correct answer clinical parameter.

* * * * *